US008046242B1

(12) United States Patent
daCosta et al.

(10) Patent No.: US 8,046,242 B1
(45) Date of Patent: Oct. 25, 2011

(54) SYSTEMS AND METHODS FOR VERIFYING PRESCRIPTION DOSAGES

(75) Inventors: Patricia A. daCosta, Marietta, GA (US); Roger Pinsonneault, Alpharetta, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 268 days.

(21) Appl. No.: 12/357,882

(22) Filed: Jan. 22, 2009

(51) Int. Cl.
*G06Q 50/00* (2006.01)

(52) U.S. Cl. .................................. 705/2; 705/3; 600/300

(58) Field of Classification Search .................. 705/2, 3; 600/300
See application file for complete search history.

(56) References Cited

U.S. PATENT DOCUMENTS

| | | | |
|---|---|---|---|
| 4,547,851 A | 10/1985 | Kurland | |
| 5,048,870 A | 9/1991 | Mangini et al. | |
| 5,235,702 A | 8/1993 | Miller | |
| 5,301,105 A | 4/1994 | Cummings | |
| 5,359,509 A | 10/1994 | Little et al. | |
| 5,544,044 A | 8/1996 | Leatherman | |
| 5,550,734 A | 8/1996 | Tarter et al. | |
| 5,628,530 A | 5/1997 | Thornton | |
| 5,644,778 A | 7/1997 | Burks et al. | |
| 5,704,044 A | 12/1997 | Tarter et al. | |
| 5,737,539 A | 4/1998 | Edelson et al. | |
| 5,740,268 A | 4/1998 | Nishikawa et al. | |
| 5,748,907 A | 5/1998 | Crane | |
| 5,749,907 A | 5/1998 | Mann | |
| 5,832,447 A | 11/1998 | Rieker et al. | |
| 5,845,255 A | 12/1998 | Mayaud | |
| 5,892,900 A | 4/1999 | Ginter et al. | |
| 5,915,971 A * | 6/1999 | Ramsay et al. | 434/276 |
| 5,950,169 A | 9/1999 | Borghesi et al. | |
| 5,950,630 A * | 9/1999 | Portwood et al. | 128/897 |
| 5,956,736 A | 9/1999 | Hanson et al. | |
| 5,958,930 A | 9/1999 | Gangjee | |
| 5,963,915 A | 10/1999 | Kirsch | |
| 5,991,750 A | 11/1999 | Watson | |

(Continued)

FOREIGN PATENT DOCUMENTS

CA         2482370 A1    3/2006

(Continued)

OTHER PUBLICATIONS

Paul Brians, Common Errors in English Usage, Retrieved from Nov. 21, 2007.*

(Continued)

*Primary Examiner* — Gerald J. O'Connor
*Assistant Examiner* — Jonathan K Ng
(74) *Attorney, Agent, or Firm* — Sutherland Asbill & Brennan LLP

(57) ABSTRACT

Systems and methods for verifying prescription transaction dosages can be provided according to embodiments of the invention. According to one example embodiment, a method for dosage error verification may be provided. The method may include executing computer program instructions by one or more processors for receiving a prescription transaction including a submitted drug product and a submitted strength of the submitted drug product; comparing the submitted drug product and the submitted strength to dosage error data residing in a dosage error database; determining that the submitted drug product is a member of at least one dosage error pair indicated by the dosage error data; determining that the submitted strength is potentially incorrect based at least in part on strengths indicated by the at least one dosage error pair; and performing an edit action based at least in part on the determination that the submitted strength is potentially incorrect.

28 Claims, 9 Drawing Sheets

U.S. PATENT DOCUMENTS

| | | | |
|---|---|---|---|
| 6,006,242 A | 12/1999 | Poole et al. | |
| 6,012,035 A | 1/2000 | Freeman et al. | |
| 6,073,104 A | 6/2000 | Field | |
| 6,195,612 B1 | 2/2001 | Pack-Harris | |
| 6,202,923 B1 | 3/2001 | Boyer et al. | |
| 6,224,387 B1 | 5/2001 | Jones | |
| 6,272,472 B1 | 8/2001 | Danneels et al. | |
| 6,307,940 B1 | 10/2001 | Yamamoto et al. | |
| 6,324,516 B1 | 11/2001 | Shults et al. | |
| 6,330,546 B1 | 12/2001 | Gopinathan et al. | |
| 6,341,265 B1 | 1/2002 | Provost et al. | |
| 6,343,271 B1 | 1/2002 | Peterson et al. | |
| 6,427,020 B1 | 7/2002 | Rhoads | |
| 6,529,892 B1* | 3/2003 | Lambert | 706/55 |
| 6,632,251 B1 | 10/2003 | Rutten et al. | |
| 6,671,692 B1 | 12/2003 | Marpe et al. | |
| 6,671,693 B1 | 12/2003 | Marpe et al. | |
| 6,694,334 B2* | 2/2004 | DuLong et al. | 604/189 |
| 6,714,918 B2 | 3/2004 | Hillmer et al. | |
| 6,757,898 B1 | 6/2004 | Ilsen et al. | |
| 6,769,228 B1 | 8/2004 | Mahar | |
| 6,879,959 B1 | 4/2005 | Chapman et al. | |
| 6,978,286 B2* | 12/2005 | Francis et al. | 708/132 |
| 7,013,284 B2 | 3/2006 | Guyan et al. | |
| 7,028,723 B1* | 4/2006 | Alouani et al. | 141/83 |
| 7,111,173 B1 | 9/2006 | Scheidt | |
| 7,155,397 B2 | 12/2006 | Alexander et al. | |
| 7,356,460 B1 | 4/2008 | Kennedy et al. | |
| 7,380,707 B1 | 6/2008 | Fredman | |
| 7,401,027 B2 | 7/2008 | Moore et al. | |
| 7,418,400 B1 | 8/2008 | Lorenz | |
| 7,490,047 B2* | 2/2009 | Brown et al. | 705/2 |
| 7,490,049 B2* | 2/2009 | Miller et al. | 705/3 |
| 7,493,263 B2* | 2/2009 | Helmus et al. | 705/2 |
| 7,555,435 B2* | 6/2009 | Ball et al. | 705/2 |
| 7,711,583 B2* | 5/2010 | Epstein et al. | 705/3 |
| 7,716,068 B2* | 5/2010 | Ball et al. | 705/3 |
| 7,720,694 B2* | 5/2010 | Potuluri et al. | 705/2 |
| 7,801,642 B2* | 9/2010 | Ansari et al. | 700/240 |
| 2001/0001014 A1 | 5/2001 | Glendon, III et al. | |
| 2001/0032099 A1 | 10/2001 | Joao | |
| 2001/0037216 A1 | 11/2001 | Oscar et al. | |
| 2001/0037224 A1 | 11/2001 | Eldridge et al. | |
| 2001/0041993 A1 | 11/2001 | Campbell | |
| 2001/0056358 A1 | 12/2001 | Dulong et al. | |
| 2002/0002495 A1 | 1/2002 | Ullman | |
| 2002/0035488 A1 | 3/2002 | Aquila et al. | |
| 2002/0042725 A1 | 4/2002 | Mayaud | |
| 2002/0044043 A1 | 4/2002 | Chaco et al. | |
| 2002/0049617 A1 | 4/2002 | Lencki et al. | |
| 2002/0055856 A1 | 5/2002 | Adams | |
| 2002/0065687 A1 | 5/2002 | Onoue | |
| 2002/0087554 A1 | 7/2002 | Seelinger | |
| 2002/0087583 A1 | 7/2002 | Morgan et al. | |
| 2002/0111832 A1 | 8/2002 | Judge | |
| 2002/0120473 A1 | 8/2002 | Wiggins | |
| 2002/0128883 A1 | 9/2002 | Harris | |
| 2002/0133503 A1 | 9/2002 | Amar et al. | |
| 2002/0138593 A1 | 9/2002 | Novak et al. | |
| 2002/0175370 A1 | 11/2002 | Bockelman | |
| 2002/0183979 A1 | 12/2002 | Wildman | |
| 2002/0198831 A1 | 12/2002 | Patricelli et al. | |
| 2003/0009357 A1 | 1/2003 | Pish | |
| 2003/0009367 A1 | 1/2003 | Morrison | |
| 2003/0028404 A1 | 2/2003 | Herron et al. | |
| 2003/0050799 A1 | 3/2003 | Jay et al. | |
| 2003/0074222 A1 | 4/2003 | Rosow et al. | |
| 2003/0083903 A1 | 5/2003 | Myers | |
| 2003/0120588 A1 | 6/2003 | Dodd et al. | |
| 2003/0149594 A1 | 8/2003 | Beazley et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0006490 A1 | 1/2004 | Gingrich et al. | |
| 2004/0019464 A1 | 1/2004 | Martucci et al. | |
| 2004/0039599 A1 | 2/2004 | Fralic | |
| 2004/0046020 A1 | 3/2004 | Andreasson et al. | |
| 2004/0059600 A1 | 3/2004 | Ball | |
| 2004/0059601 A1 | 3/2004 | Ball | |
| 2004/0059602 A1 | 3/2004 | Ball | |
| 2004/0059607 A1 | 3/2004 | Ball | |
| 2004/0073457 A1 | 4/2004 | Kalies | |
| 2004/0078234 A1 | 4/2004 | Tallal, Jr. | |
| 2004/0093242 A1 | 5/2004 | Cadigan et al. | |
| 2004/0111291 A1 | 6/2004 | Dust et al. | |
| 2004/0117323 A1 | 6/2004 | Mindala | |
| 2004/0148198 A1 | 7/2004 | Kalies | |
| 2004/0172281 A1 | 9/2004 | Stanners | |
| 2004/0188998 A1 | 9/2004 | Henthorn | |
| 2004/0249745 A1 | 12/2004 | Baaren | |
| 2005/0015280 A1 | 1/2005 | Gabel et al. | |
| 2005/0033604 A1 | 2/2005 | Hogan | |
| 2005/0060201 A1 | 3/2005 | Connely, III et al. | |
| 2005/0065821 A1 | 3/2005 | Kalies | |
| 2005/0102169 A1 | 5/2005 | Wilson | |
| 2005/0125292 A1 | 6/2005 | Kassab et al. | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0085230 A1 | 4/2006 | Brill et al. | |
| 2006/0136268 A1* | 6/2006 | Ash et al. | 705/3 |
| 2006/0149784 A1 | 7/2006 | Tholl et al. | |
| 2006/0184391 A1 | 8/2006 | Barre et al. | |
| 2006/0247948 A1 | 11/2006 | Ellis et al. | |
| 2006/0259363 A1 | 11/2006 | Jhetam et al. | |
| 2006/0271405 A1 | 11/2006 | Cipolle et al. | |
| 2007/0005402 A1 | 1/2007 | Kennedy et al. | |
| 2007/0050209 A1 | 3/2007 | Yered | |
| 2007/0100662 A1* | 5/2007 | Suwalski et al. | 705/2 |
| 2007/0136100 A1 | 6/2007 | Daugherty et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2008/0262868 A1* | 10/2008 | Malolepszy | 705/2 |
| 2008/0312957 A1* | 12/2008 | Luciano et al. | 705/2 |

FOREIGN PATENT DOCUMENTS

| | | |
|---|---|---|
| EP | 1310895 A2 | 11/2002 |
| WO | WO 9106917 A1 | 5/1991 |
| WO | WO 9503569 A3 | 2/1995 |
| WO | WO 9725682 A1 | 7/1997 |
| WO | WO 9850871 A1 | 11/1998 |
| WO | WO 0039737 A1 | 7/2000 |
| WO | WO 2007025295 A2 | 3/2007 |

OTHER PUBLICATIONS

U.S. Appl. No. 12/121,495, filed May 15, 2008, Ball.

Untitled Webpage, "Apparatus, Method and Product for Multi-attribute Drug Comparison to Avoid Medical Errors" University of Illinois at Chicago, pp. 1-2, available at www.uic.edu.

1998 Conference Archive, "Enhancing Patient Safety and Reducing Errors to Health Care", pp. 1-9, available at www.npsf.org.

A Publication of the USP Practitioner's Reporting Network, "USP Quality Review", U.S. Pharmacopeia, No. 66, May 1999.

Webpage entitled: Institute for Safe Medication Practices, "Prescription mapping can improve efficiency while minimizing errors with look-alike products", available at www.ismp.org.

Webpage entitled: ISMP Quarterly Action Agenda: Oct.-Dec. 2001, Jan. 23, 2002; pp. 1-3, available at www.ismp.org.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . . " Patient Safety & Quality Healthcare [Online] Aug. 2005. URL:http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005.

PR Newswire, "NDCHealth Annouces NDC Rx Safety Advisor to Help Prevent Look-Alike Sound-Alike Dispensation Errors", New York: Aug. 12, 2002.p. 1.

FDa Alert, Aug. 8, 2008 DRUGS, Information for Healthcare Professionals—Simvastatin (marketed as Zocor and generics), Ezetimibe/Simvastatin (marketed as Vytorin), Niacin extended-release/Simvastatin (marketed as Simcor), used with Amiodarone (Cordarone, Pacerone), obtained from fda.gov/Drugs/DrugSafety Website on Sep. 15, 2009.

Drug Sheet entitled: Generic Name: lovastatin, Brand Name: Mevacor, Altoprev.

Anonymous, Recommendations for the Use of 3-Hydroxy-3-methylglutaryl Coenzyme A Reductase Inhibitors (statins) i Veteran Patients Receiving Medications with the Potential for Drug-Drug Interactions, Nov. 2001.

Jerilyn B. Petropoulos and Christina E. Bello-Quintero, Frequency of Simvastatin Prescriptions with Potentially Interacting Mediations in a Veterans Affairs Health Care System, Journal of Managed Care Pharmacy, pp. 239-242, vol. 10, No. 3, May/Jun. 2004.

Joseph M. Kahwaji and Ryszard R. Dudek, How Can We Manage Hyperlipidemia and Avoid Rhabdomyolysis in Transplant Patients?, The Permanente Journal/Fall 2006/vol. 10, No. 3.

Drug-Drug, Drug-Dietary Supplement, and Other Interactions, Regulatory Science.

Helen Fields, Doctors Often Ignore 'Black Box' Warnings on Prescription Drugs, Nov. 18, 2005.

How Often do Doctors Ignore Drug Interaction Warnings Generated by Electronic Prescribing Systems? Feb. 23, 2009, KevinMD.com—medical weblog.

Martin Kohl, Although There Aren't Any Perfect Solutions to Creating a Formulary Free of Drug-drug Interactions, There are Things You Can Do to Limit Problems.

Office Action dated Apr. 19, 2007, in U. S. Appl. No. 10/339,230.
Final Office Action dated Oct. 18, 2007 in U.S. Appl. No. 10/339,230.
Office Action dated Feb. 28, 2008 in U.S. Appl. No. 10/339,230.
Final Office Action dated Sep. 29, 2008 in U.S. Appl. No. 10/339,230.
Non-Final Office Action dated Mar. 27, 2009 in U.S. Appl. No. 10/339,230.
Notice of Allowance for U.S. Appl. No. 10/339,230, date mailed by USPTO, Apr. 9, 2009.
Final Office Action dated Sep. 11, 2009 in U.S. Appl. No. 10/339,230.
Office Action dated Aug. 22, 2007 in U.S. Appl. No. 10/339,000.
Office Action dated Mar. 17, 2008 in U.S. Appl. No. 10/339,000.
Final Office Action mailed Oct. 9, 2008 for U.S. Appl. No. 10/339,000.
Office Action dated Apr. 2, 2007 in U.S. Appl. No. 10/339,612.
Final Office Action dated Sep. 20, 2007 in U.S. Appl. No. 10/339,612.
Office Action dated Jan. 25, 2008 in U.S. Appl. No. 10/339,612.
Final Office Action dated Aug. 6, 2008 in U.S. Appl. No. 10/339,612.
Notice of Abandonment for Failure to Respond to Office Action for U.S. Appl. No. 10/339,612 mailed Mar. 31, 2009.
Office Action dated Jun. 21, 2005, in U.S. Appl. No. 10/339,108.
Office Action Dated Sep. 16, 2005, U.S. Appl. No. 10/339,108.
Final Office Action dated Mar. 16, 2006 in U.S. Appl. No. 10/339,108.
Final Office Action dated Sep. 7, 2006 in U.S. Appl. No. 10/339,108.
Office Action Dated Mar. 5, 2007, U.S. Appl. No. 10/339,108.
Final Office Action dated Aug. 23, 2007 in U.S. Appl. No. 10/339,108.
Notice of Abandonment for Faliure to Respond to Office Action for U.S. Appl. No. 10/339,108 mailed Nov. 4, 2008.
Non-Final Office Action for U.S. Appl. No. 12/121,495 mailed Apr. 12, 2011.
Final Office Action for U.S. Appl. No. 12/357,882 mailed Apr. 13, 2011.

* cited by examiner

SYSTEMS AND METHODS FOR VERIFYING PRESCRIPTION DOSAGES

FIELD OF THE INVENTION

Aspects of the invention relate generally to prescription processing systems, and more particularly, to systems and methods for verifying prescription dosages.

BACKGROUND OF THE INVENTION

Medication errors are increasingly recognized as an important cause of preventable deaths and injuries. A significant percentage of medication errors occur when a prescribed strength of a given drug is confused with a non-prescribed strength available for the same drug, and the non-prescribed strength is dispensed to the patient. Dosages can look like other dosages when handwritten or may be mistaken for another dosage when ordered orally. Interestingly, some of the more common errors have not varied over time, according to certain studies done on prescription errors. Such errors may be occurring due to pharmacists and/or healthcare providers being under a continuous and stressful workload. As an example, a pharmacist may accept a prescription for digoxin 0.125 mg, and fill it in error with digoxin 0.25 mg. Depending upon the drug prescribed, the consequences of selecting the wrong strength could be dangerous, or even fatal, especially when the prescribed drug has a narrow margin of therapeutic safety. Another potential consequence is a lack of efficacy, such as may occur when a lower dosage is filled than what was prescribed.

Accordingly, there is a need for systems and methods that facilitate verifying prescription dosages. There is a further need for systems and methods that perform efficient and intelligent dosage verification processing by utilizing one or more of a variety of verification processing options.

SUMMARY OF THE INVENTION

Embodiments of the invention may provide systems and methods for verifying prescription transaction dosages. According to one example embodiment, a method for dosage error verification may be provided. The method may include executing computer program instructions by one or more processors for receiving a prescription transaction including a submitted drug product and a submitted strength of the submitted drug product; comparing the submitted drug product and the submitted strength to dosage error data residing in a dosage error database; determining that the submitted drug product is a member of at least one dosage error pair indicated by the dosage error data; determining that the submitted strength is potentially incorrect based at least in part on strengths indicated by the at least one dosage error pair; and performing an edit action based at least in part on the determination that the submitted strength is potentially incorrect. According to one aspect, the method may further include executing computer program instructions by one or more processors for generating a message and transmitting a message. According to another aspect, the method may further include comparing the submitted drug product and the submitted strength to patient history data for a patient residing in a patient history database; and determining that the submitted drug product and submitted strength has not previously been prescribed to the patient based on the patient history data for the patient. According to yet another aspect, the method may further include determining that a calculated daily dosage based on the submitted strength does not meet at least one of: maximum dosage criteria, minimum dosage criteria, or typical dosage criteria.

According to another example embodiment, a method for dosage error verification can be provided. The method may include executing computer program instructions by one or more processors for receiving a prescription transaction including a submitted drug product, a submitted strength of the submitted drug product, and identifying a patient to whom the submitted drug product is prescribed; comparing the submitted drug product and the submitted strength to patient history data associated with the patient and residing in a patient history database; determining that the submitted strength is potentially incorrect based at least in part on the patient history data associated with the patient; and performing an edit action based on the determination that the submitted strength is potentially incorrect. According to one aspect, the method may further include determining that the submitted drug product has been previously prescribed to the patient, but that the submitted drug product has not been prescribed to the patient in the submitted strength.

According to yet another example embodiment, a system for dosage error verification can be provided. The system may include means for receiving prescription data relating to a prescription; at least one database for storing dosage error data and patient history data; and a processor functionally coupled to the means for receiving prescription data and the at least one database. The processor may be configured for executing computer program instructions to receive a prescription transaction including a submitted drug product, a submitted strength of the submitted drug product, and identifying a patient; compare the submitted drug product and the submitted strength to the dosage error data to determine whether the submitted drug product is a member of at least one dosage error pair indicated by the dosage error data and whether the submitted strength is potentially incorrect based at least in part on strengths indicated by the at least one dosage error pair; compare the submitted drug product and the submitted strength to patient history data associated with the patient to determine whether the submitted strength is potentially incorrect based at least in part on the patient history data associated with the patient; and perform an edit action if it is determined that the submitted strength is potentially incorrect. According to one aspect, the processor may be configured for executing the computer program instructions to determine that a calculated daily dosage based on the submitted strength does not meet at least one of: maximum dosage criteria, minimum dosage criteria, or typical dosage criteria.

According to yet another example embodiment, a system for dosage error verification can be provided. The system may include means for receiving prescription data relating to a prescription; at least one database for storing dosage error data; and a processor functionally coupled to the means for receiving prescription data and the at least one database. The processor may be configured for executing computer program instructions to receive a prescription transaction comprising a submitted drug product and a submitted strength of the submitted drug product; compare the submitted drug product and the submitted strength to dosage error data residing in a dosage error database; determine that the submitted drug product is a member of at least one dosage error pair indicated by the dosage error data; determine that the submitted strength is potentially incorrect based at least in part on strengths indicated by the at least one dosage error pair; and perform an edit action based at least in part on the determination that the submitted strength is potentially incorrect.

According to yet another example embodiment, a system for dosage error verification can be provided. The system may include means for receiving prescription data relating to a prescription; at least one database for storing patient history data; and a processor functionally coupled to the means for receiving prescription data and the at least one database. The processor may be configured for executing computer program instructions to receive a prescription transaction comprising a submitted drug product, a submitted strength of the submitted drug product, and identifying a patient to whom the submitted drug product is prescribed; compare the submitted drug product and the submitted strength to patient history data associated with the patient and residing in a patient history database; determine that the submitted strength is potentially incorrect based at least in part on the patient history data associated with the patient; and perform an edit action based on the determination that the submitted strength is potentially incorrect.

According to yet another example embodiment a computer program product can be provided. The computer program product can include a computer usable medium having a computer readable program code embodied therein, the computer readable code adapted to be executed to receive a prescription transaction including a submitted drug product, a submitted strength of the submitted drug product, and identifying a patient; compare the submitted drug product and the submitted strength to the dosage error data to determine whether the submitted drug product is a member of at least one dosage error pair indicated by the dosage error data and whether the submitted strength is potentially incorrect based at least in part on strengths indicated by the at least one dosage error pair; compare the submitted drug product and the submitted strength to patient history data associated with the patient to determine whether the submitted strength is potentially incorrect based at least in part on the patient history data associated with the patient; and perform an edit action if it is determined that the submitted strength is potentially incorrect.

According to yet another example embodiment a system for dosage error verification can be provided. The system may include means for executing computer program instructions by one or more processors for receiving a prescription transaction including a submitted drug product and a submitted strength of the submitted drug product; means for comparing the submitted drug product and the submitted strength to dosage error data residing in a dosage error database; means for determining that the submitted drug product is a member of at least one dosage error pair indicated by the dosage error data; means for determining that the submitted strength is potentially incorrect based at least in part on strengths indicated by the at least one dosage error pair; and means for performing an edit action based at least in part on the determination that the submitted strength is potentially incorrect. According to one aspect, the system may further include means for executing computer program instructions by one or more processors for generating a message and transmitting a message. According to another aspect, the system may further include means for comparing the submitted drug product and the submitted strength to patient history data for a patient residing in a patient history database; and means for determining that the submitted drug product and submitted strength has not previously been prescribed to the patient based on the patient history data for the patient. According to yet another aspect, the system may further include means for determining that a calculated daily dosage based on the submitted strength does not meet at least one of: maximum dosage criteria, minimum dosage criteria, or typical dosage criteria.

Additional systems, methods, apparatus, features, and aspects are realized through the techniques of various embodiments described herein. Other embodiments and aspects are described in detail herein and are considered a part of the claimed invention. Other embodiments and features can be understood with reference to the description and to the drawings.

BRIEF DESCRIPTION OF THE DRAWINGS

Reference will now be made to the accompanying drawings, which are not necessarily drawn to scale, and wherein.

DETAILED DESCRIPTION

Figure 1:
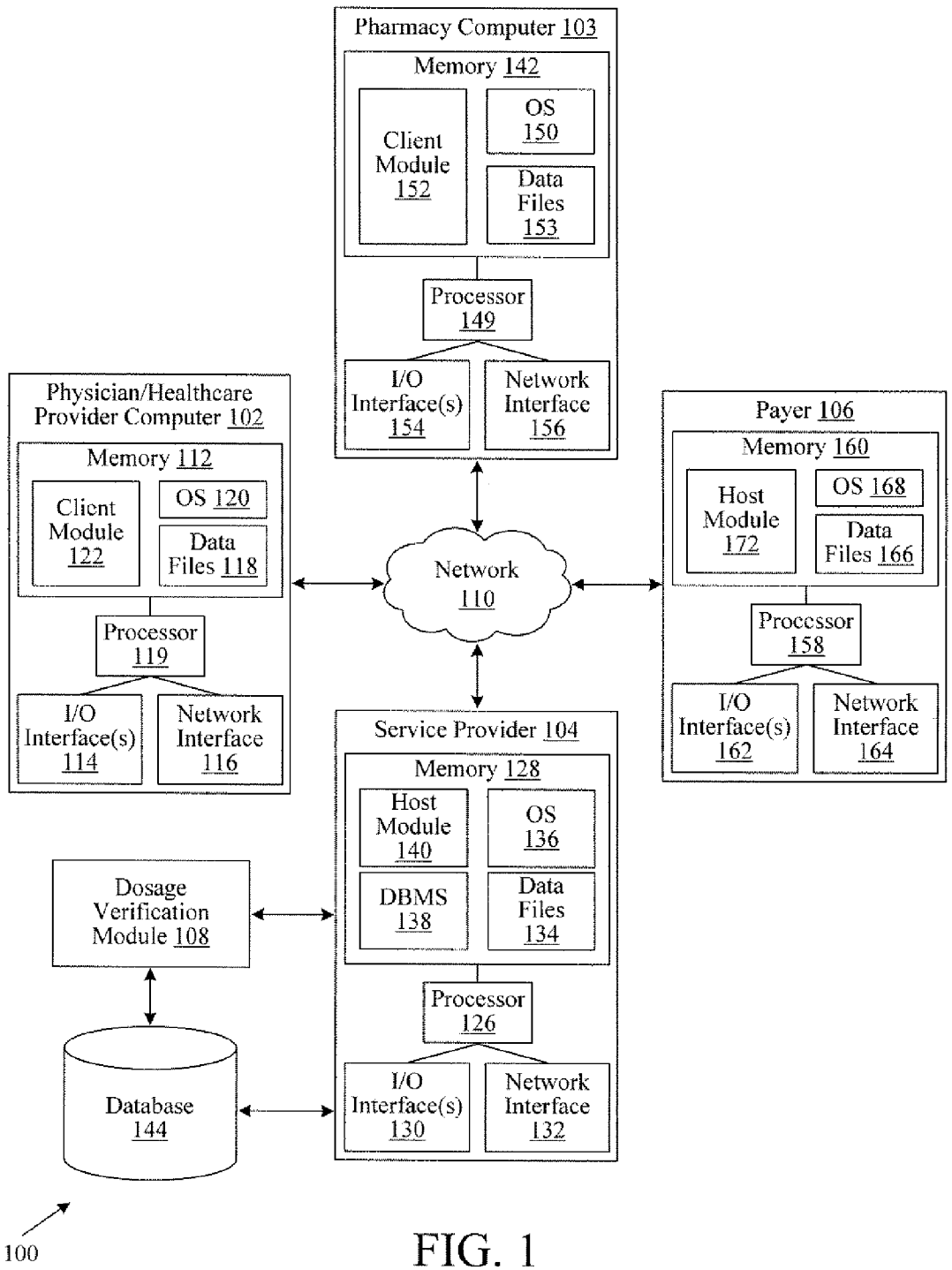
FIG. 1 illustrates an example system that is operative to facilitate dosage verification activities, according to an example embodiment of the invention.

Example embodiments of the invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Example embodiments are directed towards verifying dosages in prescription transactions. Example systems and methods provide the ability for an entity to monitor prescription transactions and return appropriate messages to pharmacists or other healthcare providers when the characteristics of a prescription transaction or other dosage, prescribing, dispensing, and/or consumption data indicate the possibility that a prescription transaction may lead to a dosing error, such as an incorrect dosage strength, dispense quantity, and/or days supply. One or more prescription transaction verification processes can be used, such as comparing a submitted drug and strength to dosage error data, such as dosage error pairs identifying counterpart strengths having a possibility of causing a dosing error, and/or comparing a submitted drug and strength combination to the patient's prescription transaction history. Additional prescription transaction processing can then be performed, such as to provide additional data for verifying the dosage, including, but not limited to, maximum dosage processing, minimum dosage processing, and typical dosage processing. Upon identifying a potential dosage error, a message can be generated and transmitted to the entity sending the prescription indicating the potential error and optionally suggesting alternative dosages. Moreover, certain embodiments provide systems and methods with additional flexibility for activating and deactivating certain verification processes, and/or weighting to emphasize or deemphasize certain verification processes. Such system and method flexibility may be adjustable by a pharmacy, by a healthcare provider, by a payer, by the entity or entities providing the verification processes, and/or by any other entities participating in prescription transaction processing.

As used herein, the terms "dosage error data" and "dosage error pair" are used to generally refer to data that may indicate that a given submitted drug and strength combination may lead to a dosing error because of a possibility that the submitted strength may be incorrect. For example, in one embodiment, dosage error pair data may indicate a pair of drugs with counterpart strengths, whereby one strength may be an error of the other or may have a high likelihood of causing a dispensing error. Accordingly, the terms "dosage error data" and "dosage error pair" are not intended to mean that a given strength pair necessarily identifies an error or otherwise incorrect strength; but may generally refer to data that may aid in determining a potential error under some circumstances.

In example embodiments, a service provider performs some or all of the dosage verification processing, receives prescription transactions from a pharmacy or a healthcare provider, interfaces with one or more payers to verify eligibility, payment, etc., and interfaces with the pharmacies or healthcare providers to update prescription transactions status, as described in more detail herein. The term "service provider" may be used herein to refer generally to any entity which may perform additional processing and/or provide additional services associated with prescription transaction processing, and may include, but is not limited to, one or more "switch providers" performing routing and processing of prescription transactions between healthcare providers (also referred to interchangeably herein as a "claims clearinghouse"), pharmacies, payers (also referred to interchangeably herein as "claims processors"), financial institutions, and/or other service providers. Though, in other embodiments, some or all of the dosage verification processing described herein may be performed by one or more other entities, such as by one or more payers (i.e., insurers), one or more pharmacies, one or more healthcare providers, and the like.

The terms "medication" and "drug" are used synonymously herein. The terms "medication name" and "drug name" may be used herein to refer generally to either a brand name or a generic name of a medication. A "drug product" is the specific item dispensed to the patient and is identified by the ingredient(s)/strength(s)/dosage form combination dispensed to patient. Drug products are commonly identified by a unique identifier, which may include, but is not limited to, a National Drug Code number ("NDC #"). A NDC # identifies the labeler/vendor, product, and trade package size. Thus, although multiple drug products may share a common ingredient(s)/strength(s)/dosage form combination, each drug product having a different brand, package size or labeler/vendor is identified by a unique NDC #. Moreover, according to example embodiments, a NDC # may represent a specific drug and strength combination, such that each strength for a given drug has a unique NDC #.

Accordingly, In various embodiments, drug products and/or drug strengths can be identified by NDC # in prescription transactions. In other embodiments, such as those involving electronic prescriptions or other types of prescription transactions, other generic product identifiers or any other data provided in one or more fields of the transaction record may be used to identify the submitted drug product and/or strength.

FIG. 1 illustrates an example system 100 that is operative to facilitate dosage verification activities, according to an example embodiment. As shown in FIG. 1, the system 100 may include a physician/healthcare provider computer 102, a pharmacy computer 103, a service provider 104, and a payer 106, which are each configured for accessing and reading associated computer-readable media having stored thereon data and/or computer program instructions for implementing the various methods described herein. Generally, network devices and systems, including the one or more physician/healthcare provider computers 102, pharmacy computers 103, service providers 104, and payers 106 may have hardware and/or software for transmitting and receiving data and/or computer program instructions over a communications link and a memory for storing data and/or computer program instructions. These network devices and systems may also include a processor for processing data and executing computer program instructions, as well as other internal and peripheral components that are well known in the art. As used herein, the term "computer-readable medium" may describe any form of memory or a propagated signal transmission medium. Propagated signals representing data and computer program instructions may be transferred between network devices and systems.

As shown in FIG. 1, the physician/healthcare provider computer 102, pharmacy computer 103, service provider 104, and payer 106 may be in communication with each other via a network 110, which, as described below, can include one or more separate or shared private and public networks, including the Internet or a publicly switched telephone network. Each of these components—the physician/healthcare provider computer 102, pharmacy computer 103, service provider 104, payer 106, and the network 110—will now be discussed in further detail.

First, the physician/healthcare provider computer 102 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, or any other processor-based device. In addition to having a processor 119, the physician/healthcare provider computer 102 may further include a memory 112, input/output ("I/O") interface(s) 114 and a network interface 116. The memory 112 may be any computer-readable medium, coupled to the processor 119, such as RAM, ROM, and/or a removable storage device for storing data files 118 and a database management system ("DBMS") to facilitate management of data files 118 and other data stored in the memory 112 and/or stored in separate databases. The memory 112 may also store various program modules, such as an operating system ("OS") 120 and a physician/provider client module 122. The OS 120 may be, but is not limited to, Microsoft Windows®, Apple OSX™, or Linux. The physician/provider client module 122 may be an Internet browser or other software, including a dedicated program, for interacting with the service provider 104 and/or pharmacy computer 103. For example, a physician or other healthcare provider may utilize the physician/provider client module 122 in providing an electronic prescription order for a patient for delivery to a designated pharmacy computer 103, either directly or via the service provider 104. The physician or other healthcare provider may utilize the physician/provider client module 122 to receive data and/or responses from the pharmacy computer 103 or service provider 104, or any other entity.

Still referring to the physician/healthcare provider computer 102, the I/O interface(s) 114 may facilitate communication between the processor 119 and various I/O devices, such as a keyboard, mouse, printer, microphone, speaker, monitor, bar code readers/scanners, RFID readers, and the like. The network interface 116 may take any of a number of forms, such as, but not limited to, a network interface card, a modem, a wireless network card, a cellular network card, and the like.

The pharmacy computer 103 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. In addition to having a processor 149, the pharmacy computer 103 may further include a memory 142, input/output ("I/O") interface(s) 154, and a network interface 156. The memory 142 may be any computer-readable medium, coupled to the processor 149, such as RAM, ROM, and/or a removable storage device for storing data files 153 and a database management system ("DBMS") to facilitate management of data files 153 and other data stored in the memory 142 and/or stored in separate databases. The memory 142 may also store various program modules, such as an operating system ("OS") 150 and a pharmacy client module 122. The OS 150 may be, but is not limited to, Microsoft Windows®, Apple OSX™, or Linux. The pharmacy client module 122 may be an Internet browser or other software, including a dedicated program, for interacting with the physician/healthcare provider computer 102, the service provider 104, and/or the payer 106. For example, a user such as a pharmacist or other pharmacy employee may utilize the pharmacy client module 122 to receive or retrieve an electronic prescription order from the physician/healthcare provider computer 102, directly or via the service provider 104. Likewise, the pharmacist or other pharmacy employee may utilize the pharmacy client module 122 in preparing and providing a prescription transaction or prescription transaction reversal to the service provider 104, such as may be for delivery to the appropriate payer 106. In example embodiments, the pharmacy client module 122 may be utilized to review prescription transaction data, such as may be provided by the service provider 104, and/or to adjust configurable parameters associated with one or more dosage verification processes performed by a service provider 104, for example. The pharmacy computer 103 may also utilize the pharmacy client module 122 to retrieve or otherwise receive data or responses from the service provider 104, or from any other entity.

Still referring to the pharmacy computer 103, the I/O interface(s) 154 may facilitate communication between the processor 149 and various I/O devices, such as a keyboard, mouse, printer, microphone, speaker, monitor, bar code readers/scanners, RFID readers, and the like. The network interface 156 may take any of a number of forms, such as, but not limited to, a network interface card, a modem, a wireless network card, a cellular network card, and the like.

The service provider 104 may include any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The service provider 104 may be configured for receiving, processing, and fulfilling requests from the physician/healthcare provider computer 102, pharmacy computer 103, and/or payer 106, relating to prescription, pharmacy, benefits, and/or claim transactions or activities. The service provider 104 may include a processor 126, a memory 128, input/output ("I/O") interface(s) 130, and a network interface 132. The memory 128 may be any computer-readable medium, coupled to the processor 126, such as RAM, ROM, and/or a removable storage device for storing data files 134 and a database management system ("DBMS") 138 to facilitate management of data files 134 and other data stored in the memory 128 and/or stored in one or more databases 144. The memory 128 may also store various program modules, such as an operating system ("OS") 136 and a service provider host module 140. The OS 136 may be, but is not limited to, Microsoft Windows®, Apple OSX™, or Linux.

The data files 134 may also store routing tables for determining the destination of communications received from the physician/healthcare provider computer 102, pharmacy computer 103, or payer 106, or any other entity. The service provider host module 140 may receive, process, and respond to requests from the respective client modules 122, 152 of the physician/healthcare provider computer 102 or pharmacy computer 103, and may further receive, process, and respond to requests from the payer host module 172 of the payer 106. The database 144 may be one or more databases operable for storing dosage error data, such as dosage error pair data, absolute dosage data, and typical dosage data, patient history data, prescription transaction data, and the like.

A dosage verification module 108 may also be operative with the service provider 104. The dosage verification module 108 may include computer program instructions for processing one or more prescription transactions, such as to verify dosages contained therein, and to generate messages, edits, and/or rejects of the prescription transactions, as described herein. In example embodiments, the dosage verification module 108 may interact with the database or databases 144 via the DBMS 138, such as to retrieve dosage error data, patient history data, and to store prescription transaction data and/or update patient history data. In one embodiment, the dosage verification module 108 and may be implemented as part of the memory 128 of the service provider 104. In another embodiment, the dosage verification module 108 may be implemented as part of a memory of a separate processor-based system. In yet other embodiments, entities other than the service provider 104 may include a dosage verification module or similar computer program instructions, enabling other entities, such as the pharmacy computer 103 or the payer 106, to perform some or all of the dosage verification processing steps described herein; however, for simplicity, the example embodiments described will describe the dosage verification processing as being performed at least in part by the service provider 104. Dosage verification processing performed at least in part by the dosage verification module is described in further detail below with reference to FIGS. 3-6.

The payer 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The payer 106 may include a processor 158, a memory 160, input/output ("I/O") interface(s) 162, and a network interface 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may also store various program modules, such as an operating system ("OS") 168 and a payer host module 172. The OS 168 may be, but is not limited to, Microsoft Windows®, Apple OSX™, or Linux. The payer host module 172 may receive, process, and respond to requests from the physician/provider client module 122 of pharmacy computer 103, and may further receive, process, and respond to requests from the service provider host module 140 of the service provider 104, or used to communicate with any other computer.

The network 110 may include any telecommunication and/or data network, whether public, private, or a combination thereof, including a local area network, a wide area network, an intranet, an internet, the Internet, intermediate hand-held data transfer devices, a publicly switched telephone network ("PSTN"), a cellular network, and/or any combination thereof and may be wired and/or wireless. The network 110 may also allow for real-time, off-line, and/or batch transactions to be transmitted between or among the physician/healthcare provider computer 102, the pharmacy computer 103, the service provider 104, and/or the payer 106. Due to network connectivity, various methodologies as described herein may be practiced in the context of distributed computing environments. It will also be appreciated that the network 110 may include a plurality of networks, each with devices such as gateways and routers for providing connectivity between or among networks 110. Instead of, or in addition to, a network 110, dedicated communication links may be used to connect the various devices in accordance with an example embodiment invention. For example, the service provider 104 may form the basis of network 110 that interconnects the physician/healthcare provider computer 102 with the pharmacy computer 103, or the pharmacy computer 103 with the payer 106.

Generally, each of the memories and data storage devices, such as the memories 112, 142, 128, 160 and the database 144, and/or any other memory and data storage device, can store data and information for subsequent retrieval. In this manner, the system 100 can store various received or collected information in memory or a database associated with one or more physician/healthcare provider computers 102, pharmacy computers 103, service providers 104, and/or payers 106. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices. In one example embodiment, for security, the service provider 104 (or any other entity) may have a dedicated connection to the database 144, as shown; though, in other embodiments, the service provider 104 or any other entity may communicate with the database 144 via a network 110.

Suitable processors, such as the processors 119, 149, 126, 158 of the physician/healthcare provider computers 102, pharmacy computers 103, service providers 104, and/or payers 106, respectively, may comprise a microprocessor, an ASIC, and/or a state machine. Example processors can be those provided by Intel Corporation (Santa Clara, Calif.), AMD Corporation (Sunnyvale, Calif.), and Motorola Corporation (Schaumburg, Ill.). Such processors comprise, or may be in communication with media, for example computer-readable media, which stores instructions that, when executed by the processor, cause the processor to perform the elements described herein. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript. Furthermore, any of the processors may operate any operating system capable of supporting locally executed applications, client-server based applications, and/or browser or browser-enabled applications.

The system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one example embodiment, the service provider 104 may be implemented as a specialized processing machine that includes hardware and/or software for performing the methods described herein. In addition, the processor and/or processing capabilities of the service provider 104, and/or the dosage verification module 108, may be implemented as part of the physician/healthcare provider computer 102, the payer 106, or any combination thereof. Accordingly, embodiments of the invention should not be construed as being limited to any particular operating environment, system architecture, or device configuration.

Figure 2A:
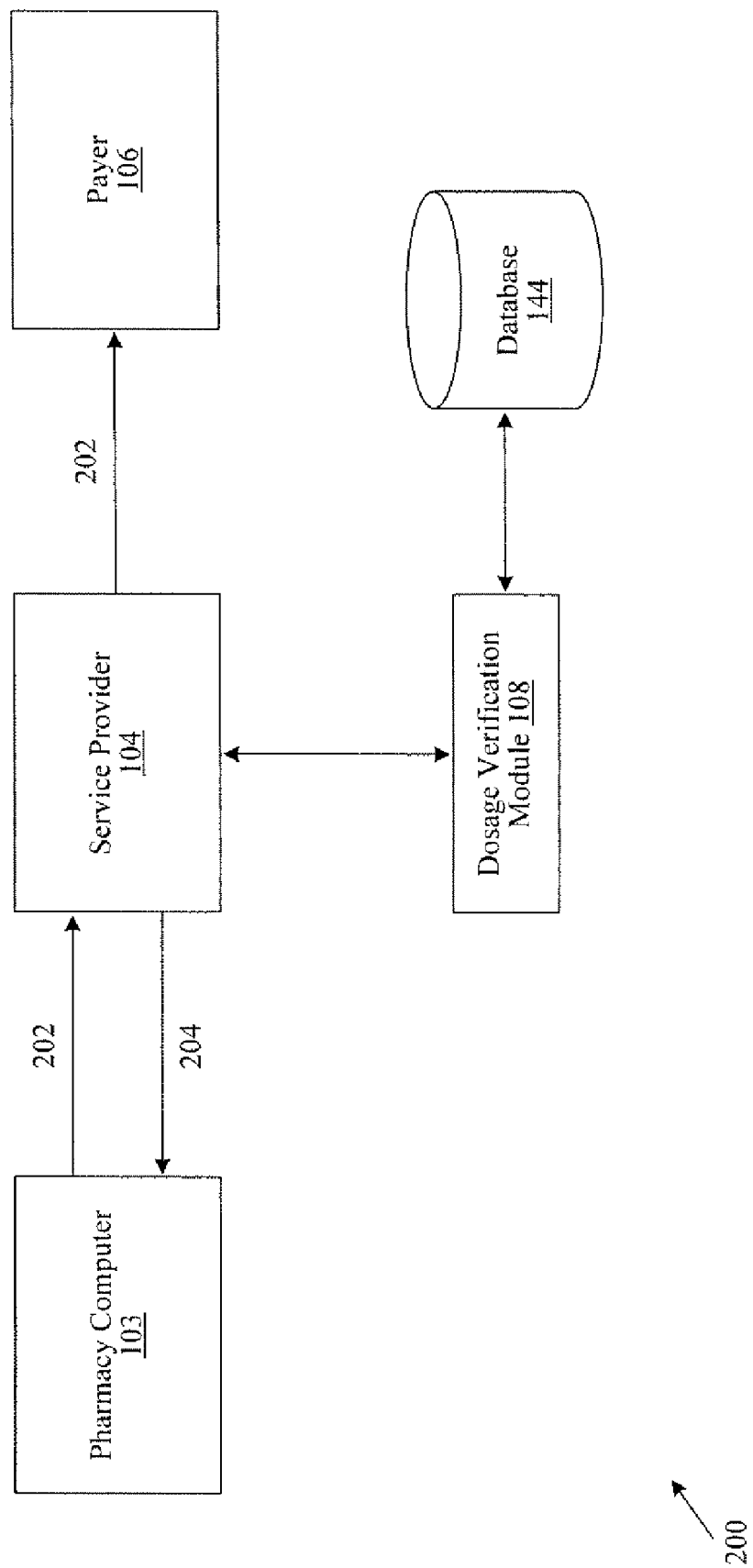
FIGS. 2A and 2B illustrate example block diagrams for prescription verification processing, according to an example embodiment of the invention.
Figure 2B:
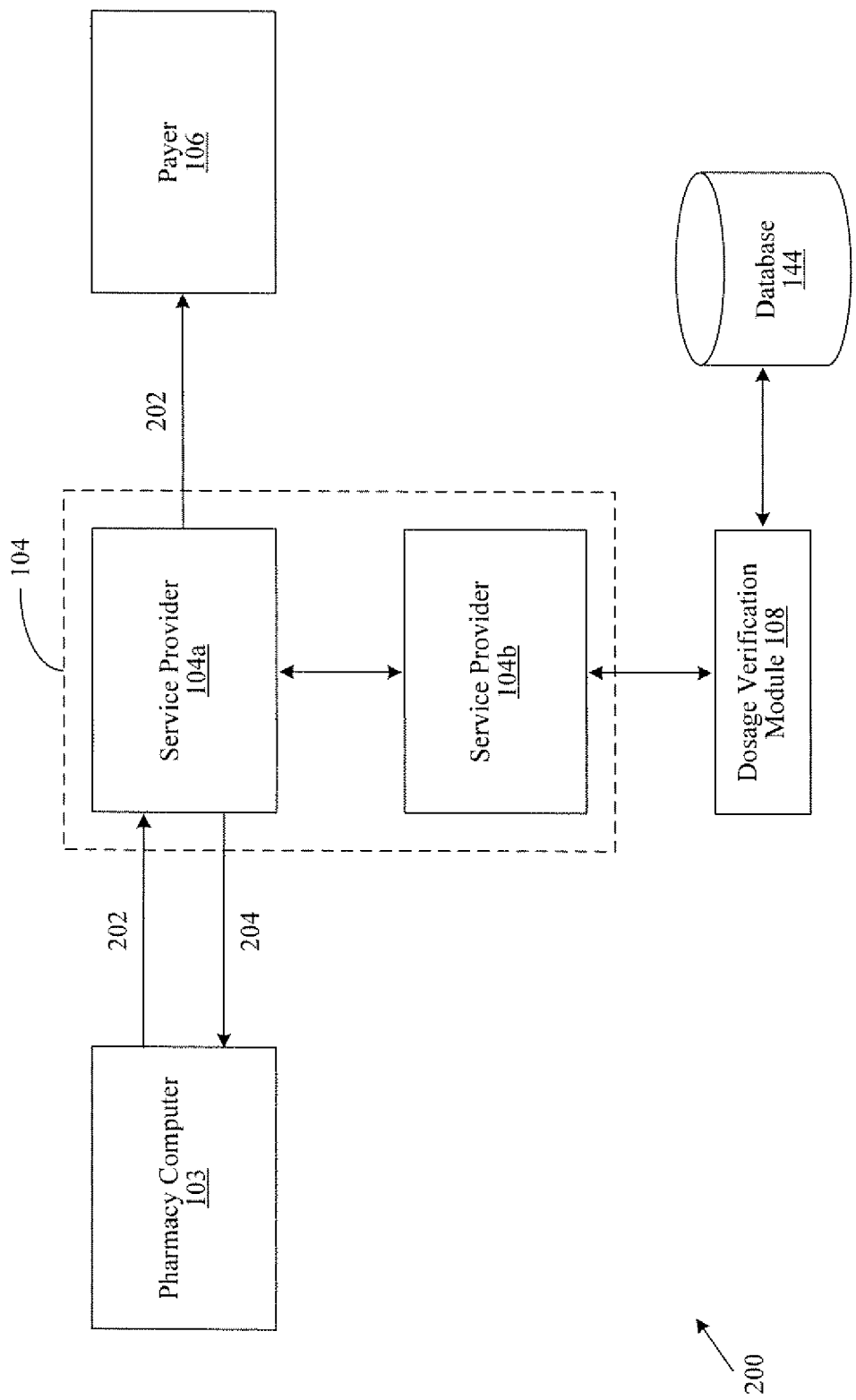

As described herein, example embodiments described herein are directed towards prescription transaction processing activities that include dosage verification. FIGS. 2A and 2B illustrate a block diagrams for dosage verification processing of a prescription transaction, according to example embodiments. With reference to an example embodiment of FIG. 2A, prescription transaction data and associated messaging may bet transmitted between one or more pharmacy computers 103, one or more service providers 104, and one or more payers 106, the components of each are described in detail with reference to FIG. 1.

Prescription transaction data can include any data that is typically provided by a patient, pharmacist, and/or other healthcare provider in relation to filling a prescription and/or requesting approval or authorization for payment from a payer. As used herein, a "claim transaction" is one example of a prescription transaction that facilitates requesting approval or authorization for payment from a payer. A payer may be an insurance company, a claims processor or adjudicator, a financial institution, or another financial service provider. Prescription transaction data may be input to the pharmacy computer 103 by a pharmacist or other healthcare provider, or may be received by the pharmacy computer 103 in electronic faun from an electronic prescription service (not shown), such as may be provided between one or more physician/healthcare provider computers 102 and one or more pharmacy computers 103. In example embodiments, the pharmacy computer 103 may be further configured for handling prescription transaction processing in addition to, or instead of, dosage verification processing. Accordingly, prescription transactions can represent prescriptions as may be written for patients, and thus can represent a physical script object, such as may be provided on paper, a label, and/or electronically. Moreover, various dosage verification processing described herein may represent a transformation of the underlying prescription object, such as to edit, update, and/or provide additional data for the prescription.

Still with reference to FIG. 2A, in one embodiment, the pharmacy computer 103 may transmit one or more prescription transactions 202 to service provider 104 for processing. Prescription transactions can be electronic records or messages intended to facilitate the communication of prescription information and/or represent the underlying prescription written for a patient. For example, prescription transactions can be used to represent and communicate prescription claim data between pharmacies and payers. Although prescription claim transactions will be discussed hereinafter, it will be understood that various embodiments may be practiced in connection with other types of prescription transactions or independently of prescription transactions (e.g., raw prescription data). The content and format of a prescription transaction may vary depending on which standard or protocol is used. In general, however, prescription claim transactions can include, but are not limited to, the drug product to be dispensed (e.g., by NDC #), which may also be referred to herein as the "submitted drug product," the submitted drug strength, the quantity to be dispensed, the days supply, patient identifier, whether the prescription claim relates to a new prescription or a refill prescription, and/or billing-related information.

According to an example embodiment, the prescription transaction 202 received by the service provider 104 may be in accordance with a version of the National Council for Prescription Drug Programs, Inc. ("NCPDP") Telecommunication Standard, although other standards may be utilized as well (e.g., the NCPDP Script Standard). An example prescription claim in accordance with a version of the NCPDP Telecommunication Standard, may include, but is not limited to, one or more of the following information:

Patient Information
    a. Name (e.g., Patient Last Name, Patient First Name, etc.)
    b. Gender
    c. Patient Address (e.g., Street Address, Zip Code, etc.)
    d. Patient Contact Information (e.g., Patient Telephone Number)
    e. Patient ID or other identifier
Insurance/Coverage Information
    a. Cardholder Name (e.g., Cardholder First Name, Cardholder Last Name)
    b. Cardholder ID or other identifier
Prescriber Information
    a. Primary Care Provider ID or other identifier (e.g., NPI code)
    b. Primary Care Provider Name (e.g., Last Name, First Name)
    c. Prescriber ID or other identifier (e.g., NPI code)
    d. Prescriber Name (e.g., Last Name, First Name)
    d. Prescriber Contact Information (e.g., Telephone Number)
Pharmacy Provider Information
    a. Pharmacy ID (e.g., NPI code)
Claim Information
    a. Drug or product information (e.g., National Drug Code (NDC))
    b. Date Prescription Written
    c. Quantity Dispensed
    d. Number of Days Supply
    e. Diagnosis/Condition
    f. Fill Number (e.g., New or Refill)
    g. Pricing information for the drug or product
Date of Service.

It will be appreciated that, while some example information has been illustrated as an example prescription claim transaction, other information may be included, instead of or in addition to that described, without departing from example embodiments. In addition, while drug product and strength values may be specified in the prescription transaction (e.g., NDC), daily dosage values and other drug data may need to be derived from the prescription data. For example, the prescription transaction may include an NDC# or other code to identify the submitted drug product and strength, upon which the submitted NDC# is mapped to a drug product. The prescription transaction data may also identify a quantity to be dispensed and a days supply, from which a submitted daily dosage value can be derived.

Prescription transactions 202 may be transmitted from the pharmacy computer 103 to the service provider 104 in batch, real-time, or near real-time. In certain embodiments, the service provider 104 may serve as a clearinghouse for multiple payer systems 106. In its capacity as a clearinghouse, the service provider 104 is operable to parse prescription transactions and forward them to the appropriate payers 106 for processing.

In serving as a clearinghouse, the service provider 104 may also be configured for performing additional pre-processing and post-processing of prescription transactions. Pre-processing and post-processing refers to real-time or near real-time validation and management of prescription data in order to maximize prescription claim reimbursement, minimize claim submission errors, and to reduce improperly filled prescriptions which may result in ineffective dosages or dangerous dosages.

According to one embodiment, upon receiving the prescription transaction 202, the service provider 104 and its associated dosage verification module 108 may perform dosage verification processing on the prescription transaction 202 data, such as, but not limited to, comparing to the prescribed patient's history, which may be stored in a patient history database or respective data tables associated with the database 144, comparing to dosage error data, which may be stored in a dosage error database or respective data tables associated with the database 144, compare to maximum dosages for the submitted drug, compare to minimum dosages for the submitted drug, and/or compare to typical dosages for the submitted drug.

In one example embodiment, a dosage error database is used to store and maintain information indicating known or derived drug product and drug strength combinations (e.g., drug name and [x] mg) that may be prone to error during prescription claim processing. Comparing the submitted drug and submitted strength received in a prescription transaction to data identifying potential error prone combinations enables the service provider 104 to better identify any potential drug strength errors that may have been entered into the prescription transaction.

In one example embodiment, dosage errors may result from certain drug and strength combinations that have the potential to result in error between other available strengths for the same drug. For example, digoxin is available and prescribed in both 0.125 mg and 0.25 mg strengths. For various reasons, as discussed further herein, an incorrect strength may be indicated in the prescription transaction data. Accordingly, a list of dosage error pairs, indicating a drug and at least two dosage strengths that may be confused, can be stored in the dosage error database to aid in dosage verification processing. The dosage error pairs may be identified and/or defined by various means, including, but not limited to, historical research, statistical studies, analysis of past prescription claim errors, reviewing drug information (e.g., Facts and Comparisons® data), manually compiling lists based on known causes for typical errors. In example embodiments, the service provider 104 (or any other entity) may update the dosage error database based on dosage verification processing performed and the responses received from pharmacies to error messages generated, which may be helpful to identify new dosage error pairs, removing dosage error pairs, and the like. In one embodiment, service provider 104 updates may be performed in real-time or near real-time, enabling the dosage error data to "learn" and acquire intelligence based on actual prescription transactions. Dosage error pairs may also be defined or identified by an industry standards organization, such as The Institute for Safe Medication Practices ("ISMP"), The United States Food and Drug Administration ("FDA"), The United States Pharmacopeia ("USP"), The Center for Drug Evaluation and Research ("CDER") of the FDA, and/or defined or identified by pharmaceutical companies, pharmacy managers, healthcare providers, service providers, and the like. Table I illustrates example dosage error pairs, as may be stored in a dosage error database, according to one embodiment.

TABLE I

Example Dosage error pairs

| Drug/First Strength | Drug/Second Strength |
|---|---|
| Abilify 2 mg | Abilify 10 mg |
| Abilify 2 mg | Abilify 20 mg |
| Anafranil 25 mg | Anafranil 75 mg |
| Clozaril 12.5 mg | Clozaril 25 mg |
| Cytomel 5 mcg | Cytomel 50 mcg |
| Digitek (Lanoxin) 0.125 mg | Digitek 0.25 mg |
| Esclim transdermal 5 mg | Esclim transdermal 15 mg |
| Humalog | Humalog mix 50/50 |
| Lexxel 5 mg/12.5 mg | Lexxel 5 mg/25 mg |
| Metolazone (Mykrox) 0.5 mg rapid-dissolve | Metolazone ( Zaroxylyn) 5 mg slow-acting |
| Topamax 15 mg | Topamax 50 mg |
| . . . | . . . |

As can be seen by the examples in Table I, drug strengths may be confused or incorrectly entered in a prescription transaction for a variety of reasons. Example error types for incorrectly entered or confused drug strength may include, but are not limited to, when one strength is a multiple of ten of another strength, when there is a single digit difference between strengths, a trailing zero after a decimal point of one strength that may be misinterpreted as occurring before the decimal point, no leading zero is provided before the decimal point causing the decimal point to be omitted, a character in the drug name that may be misidentified as a digit in the drug strength, digit/character similarities between strengths, or even spoken similarities between strengths. As used herein the terms "counterpart strength" and "alternate strength" are used interchangeably to generally refer to a strength other than the submitted strength, such as may be provided in a dosage error pair.

The following examples reference the example dosage error pairs of Table I to further explain example reasons and error types for dosage errors. Abilify 2 mg may be confused as Abilify 20 mg because 20 mg is a multiple of ten of 2 mg, and hastily entered or spoken prescription data may confuse these two. Digitek 0.125 mg may be confused with Digitek 0.25 mg, having only a single digit difference such that the "1" may be overlooked and/or omitted. If Cytomel 5 mcg was entered as "Cytomel 5.0 mcg" with a trailing zero after the decimal point, then it may be prone to be confused with Cytomel 50 mcg if the decimal point is overlooked and omitted when entering the prescription data. Similarly, Metolazone 0.5 mg may be incorrectly entered as Metolazone 5 mg if entered as "Metolazone 0.5 mg" without the leading zero before the decimal point. Confusing the digit "1" with last character "1" in Clozaril 12.5 mg (and overlooking the decimal point) may cause Clozaril 25 mg to be entered in a prescription data. Alternatively, confusing the last character "1" in Esclim transdermal 5 mg as a digit "1" could result in Esclim transdermal 15 mg being entered. Similarly, Lexxel 5 mg/1.25 mg could be entered as Lexxel 5 mg/25 mg if the separator "/" and the "1" are confused. Anafranil 25 mg may be entered as Anafranil 75 mg if the digit "2" is confused with the digit "7" due to their similar appearance. If prescription data is entered listening to the drug and strength, Topamax 50 mg may be entered as Topamax 15 mg. Moreover, certain strength and/or drug descriptors may even be omitted in haste, such as entering an intended prescription for Humalog mix 50/50 simply as Humalog in prescription data.

The data represented by Table I and described as being stored in the dosage error database, such as dosage error pairs, may not be the only data stored in the dosage error database, and is not intended to limit the way in which dosage error data is stored and/or represented. For example, in one embodiment, dosage error "pairs" may have more than two associated drug and strength combinations, such as if there were multiple related potential errors with one drug and similar strengths. In another example, additional data may be stored, such as drug and strength combinations which are indicated as highly likely to be an error, such as drug and strength combinations that are not commercially available or very rarely prescribed, for example. In one example embodiment, the dosage strength that is a highly likely (or known) dosage error can also be referred to as an "error strength," indicating that the strength is likely an incorrect dosage. Thus, if a prescription transaction includes a drug and strength combination indicated as highly likely to be an error, the dosage verification module 108 may automatically generate an error message and/or store transaction information for subsequent review, and optionally indicate the error strength, and/or indicate the counterpart strength which may be assumed to be the suggested strength. Conversely, one or more drug strength combinations may be stored, where one drug and dosage strength combination of the pair is labeled as an "likely strength," due to its counterpart being identified as highly likely being an error strength (or a known error) or the likely strength being a more typically prescribed strength. Suggested strengths, likely strengths, and error strengths may be determined empirically, or may be manually identified based on actual experience, such as frequently identified error strengths, or known information, such as strengths that are no longer available, etc.

In yet another example, the entries in the dosage error database may be weighted or ranked, such as to promote more precise and/or reliable messaging. For example, an entity may opt to give a greater weighting to dosage error pairs that have a greater statistical chance of being an error (e.g., submitted drug strength is for a valid, but very infrequently prescribed, dosage, while the counterpart is for a frequently prescribed strength), than to dosage error pairs that have a lower chance of being an error (e.g., both strengths are commonly prescribed). In other examples, an entity may opt to give a greater weighting to dosage error pairs that include a dangerous or lethal combination, or an expensive combination. Thus, the weighting can be used to attribute an overall value to the comparison of the prescription transaction to the dosage error pair, which may be considered by the dosage verification module 108 when determining whether or not to message the pharmacy (e.g., only those with a value greater than 30 on a scale from 0 to 100). These examples are not intended to be limiting, and are not intended to be required steps in the dosage verification processing using the dosage error database.

In other example embodiments, the dosage verification module 108 may also include error type algorithms to identify the possibilities of one or more of these error types (or any other error type that may be algorithmically identified) as potentially occurring based on a submitted strength extracted from the prescription transaction 202. For example, error type algorithms may identify the submitted strength as including a number that may be confused with another number, or that may sound like another number, or that may be a common multiple of ten (e.g., 10, 100, 20, 200, etc.), or a submitted drug name that ends in a confusing character (e.g., "1"), or any other error types as described herein or otherwise discovered. In one embodiment, upon identifying that the submitted strength (or drug name) contains characters or digits that are error prone, additional dosage verification processing may be performed, such as comparing to a dosage error pair list, comparing to patient history data, performing maximum/minimum dosage processing, determining if the prescription is new or a refill, and/or performing typical dosage processing, to determine with a better level of success whether a strength error is likely before messaging the pharmacy (or other entity). Though, in other embodiments, simply identifying error prone types using error type algorithms may be sufficient to generate and transmit a message to the pharmacy requesting that they confirm the dosage.

Moreover, similar processing may be performed on other dosage related values entered in prescription transactions, such as days supply and quantity dispensed, which may also be used to calculate the submitted daily dosage. For example, dosage error data may include known daily dosages, days supply, and/or quantity dispensed, for certain drug products, or even potential error pairs including this data, which may be interrogated and compared to the submitted information of prescription transaction claims to identify potential errors in these values as well.

In one example embodiment, a patient history database is used to store and maintain information related to patients' prescription transaction history, which may serve to facilitate identifying correct or potentially incorrect prescription data. The patient history database may be generated and maintained when any prescription transactions are submitted through the service provider 104, capturing patient-specific information and prescription-specific information. For example, entries in the patient history database may include personal and/or medical information pertaining to patients, such as, but not limited to, patient name, patient address, patient contact information, patient date of birth, patient age, patient sex, patient height, patient weight, known ailments or other medical conditions (past and existing), and the like. In addition, the patient history database may include records identifying previous prescription transactions, which include, but are not limited to, drug product and drug strength (both of which may be stored separately by name or the combination referenced by NDC# or by another identifier), days supply, quantity, drug usage, whether refills are authorized, prescription date, fill date, pick-up date, prescriber (e.g., physician or other healthcare provider) information, and the like. The prescription transactions may be linked to the respective patients to whom they were prescribed by a patient identifier or other unique identifier.

Accordingly, upon receiving a prescription transaction 202 and/or upon identifying the existence of a dosage error pair counterpart for a submitted strength, the dosage verification module 108 may compare the submitted drug and strength to entries in the patient history database to determine whether the same drug and strength combination has been previously prescribed for the patient. In one embodiment, the dosage verification module 108 and/or the service provider may perform additional processing, such as cross-referencing or performing additional inquiries, to determine whether an equivalent or substantially similar drug and strength combination has been previously prescribed. According to one embodiment, if the drug and strength combination has been previously prescribed for the patient, then it may be determined that the combination is valid and an edit action and/or error message need not be generated. In other embodiments, however, that the patient has been prescribed the same drug and strength combination may not be dispositive, and additional dosage verification processing may be performed and/or a warning message may still be transmitted.

Patient information stored in the patient history database may also be used to perform additional verification of the submitted drug dosage. For example, the patient's age, sex, weight, and/or height may be used to determine whether the submitted dosage is typically prescribed for a patient of that age, sex, and/or size. Such information may be programmatically stored in the database 144 or other data storage devices of the service provider 104, or may be available over a network, such as the Internet.

As further described herein, the database 144 may include additional data to facilitate other dosage verification processing, such as, but not limited to, maximum/minimum dosage processing and typical dosage processing, and other prescription processing may be performed by the service provider 104 (or any other entity) upon receiving the prescription transaction 202. The database 144 may also store reports and other data relating to the results of the dosage verification processing (and other processing). The database 144 may of course also store any other data used or generated by the service provider 104, such as data used in other pre-processing and post-processing methods and reports generated thereby.

In various embodiments, as part of the dosage verification processing, if one or more of the comparisons or other inquiries indicate that the submitted strength may be incorrect, then one or more edit actions may be performed by the dosage verification module 108. As further described herein, example edit actions may include generating and transmitting a message to the pharmacy (or other transmitting entity), informing it of a potential error. Optionally, the dosage verification module may provide alternative suggestions, generate and transmit a rejection of the prescription transaction, edit the prescription transaction prior to processing with the payer, and/or store the potentially incorrect and/or suggested updates for subsequent review, reporting, or for use in subsequent transactions.

In the case where the service provider 104 functions as a clearinghouse, the dosage verification processing may be implemented as part of the pre-processing and/or post-processing methods. In other embodiments, the service provider may not serve as a clearinghouse for prescription claim transactions and may be dedicated to performing such tasks as dosage verification processing (or other prescription error processing).

As illustrated by FIG. 2A, if the service provider 104 and its associated dosage verification module 108 do not determine that a potential error in the submitted dosage may exist in the prescription transaction (or other prescription transaction errors as may be performed), then the service provider may forward the prescription transaction 202 to a payer 106 for processing. Additional approval, authorization, or rejection messages may be returned from the payer 106 to the service provider 104, which may then transmit the messages to the pharmacy computer 103 and/or update data stored in a database 144 for reporting or future analysis. However, if it is determined that the prescription transaction may include an incorrect dosage, the service provider may transmit a verification or error message 204 to the pharmacy computer 103 as part of an edit action performed by the dosage verification module. As further described herein, the message may include information from the submitted prescription transaction, reasons for the potential error, suggested alternatives, patient history information, and the like.

In another embodiment, the prescription transaction 202 transmitted from the pharmacy computer 103 may be used to generate and/or update a patient history database, such as may be associated with the database 144 of the service provider 104. For example, upon receiving prescription transactions 202, the service provider 104 may extract information and store in a patient history database for future analysis. In example embodiments, the patient history database is updated to indicate successful, filled prescription transactions, including drug product, strength, dosage, days supply, quantity filed, and the like, such that the patient history data can be reviewed when processing subsequent prescription transactions for the same patient (or for different patients in other embodiments). In another example, the prescription transaction 202 received from the pharmacy may be for a prescription reversal, such as if an earlier requested prescription was not distributed to the patient or otherwise not filled for any other reasons. In this example, the service provider 104 may extract information from the prescription transaction 202 and update the patient history database to reflect that a previously entered transaction was not actually filled and should not be recognized as a valid historical patient prescription. This functionality may be useful when comparing subsequently received prescription transactions to the patient history database, providing accurate information therein.

It will be appreciated that variations of FIG. 2A may be available in accordance with other example embodiments. For example, FIG. 2B illustrates a variation of the block diagram of FIG. 2A. As shown by FIG. 2B, the service provider 104 may be comprised of two or more distinct service providers 104a and 104b that are in communication with each other. Service provider 104a may be operative with the pharmacy computer 103 and the payer 106, while the service provider 104b may be operative with other pharmacy computers and payers. However, the service provider 104b may have a data processing arrangement with the service provider 104a. Under the data processing agreement, the service provider 104a may be permitted to utilize or offer services of the service provider 104b, including the dosage verification module 108 and the database 144. Accordingly, the services of the service provider 104b, including the dosage verification module 108 and the database 144, may be available via the service providers 104a and 104b.

In other embodiments, one or more of the dosage verification processing functions described herein, and/or any of the associated data, may be performed and/or maintained by other entities of the system, such as in a distributed system in which the pharmacy computer 103 and/or the payer 106 are operable to perform some or all of the dosage verification processing. In yet another embodiment, the service provider 104 may be in communication with one or more physicians or healthcare providers, and may receive, process, and transmit prescription transactions between the physicians or healthcare providers and one or more pharmacy systems, such as in an electronic prescribing system. Other variations are possible in other embodiments, and should still be considered within the scope of that described herein.

Figure 3:
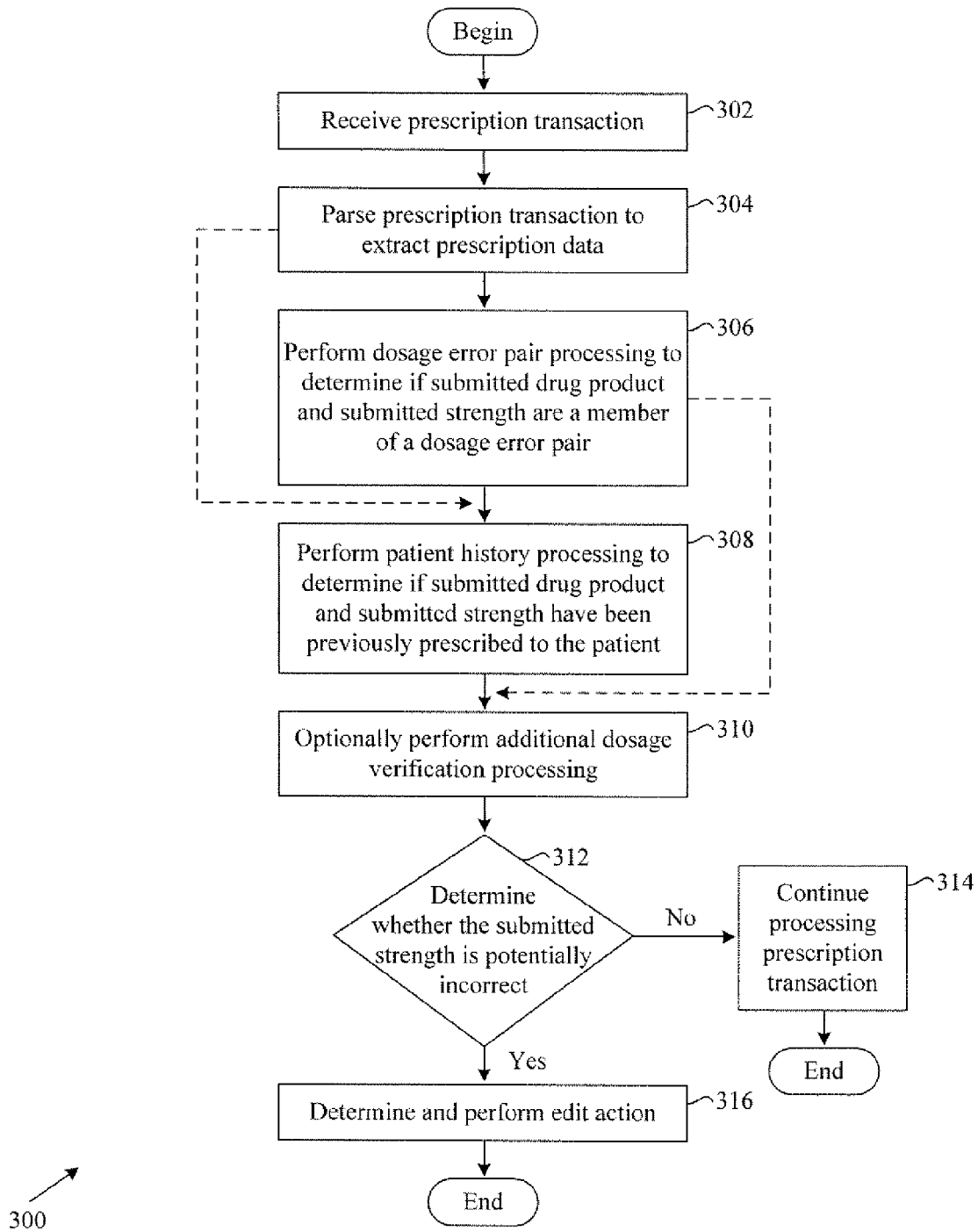
FIG. 3 illustrates an example flow diagram for performing dosage verification processing on a prescription transaction, according to one example embodiment.

FIG. 3 illustrates a flow diagram of an example method 300 for performing dosage verification processing on a prescription transaction, according to one example embodiment. As illustrated by this example method 300, example embodiments may include performing dosage verification by a dosage verification module, such as the dosage verification module 108 described with reference with FIGS. 1-2, including one or both of dosage error pair processing and patient history processing to determine whether the prescription transaction may include potentially incorrect dosage data.

The method 300 begins at block 302. At block 302, a service provider may receive a prescription transaction, such as the service provider 104 as described with reference to FIGS. 1-2. In one example embodiment, the service provider may receive the prescription transaction over a network from a pharmacy computer, such as the pharmacy computer 103 as described with reference to FIGS. 1-2. Though, in other example embodiments, the service provider may receive a prescription transaction from another entity, for example, directly from a physician/healthcare provider, or over a network directly from a patient, which may occur when a patient files a claim directly with a payer or when verifying eligibility or benefits related to a particular prescription.

Upon receiving the prescription transaction, block 304 follows, in which the prescription transaction may be parsed to extract prescription data from the transaction. The data extracted may include, but is not limited to, the submitted drug product, the submitted strength, a patient identifier, whether the transaction relates to a new prescription or a refill, and the like. Other additional prescription data and/or patient data, such as is described with reference to FIG. 2A, may also be extracted. For example, when building a patient history database, additional patient data and prescription data may be extracted. Moreover, in example embodiments, the service provider 104 may have to perform additional processing and calculation on the extracted prescription data, such as when determining the submitted daily dosage from the strength, days supply, and quantity.

Following block 304 is block 306, in which the submitted drug product and submitted strength may be compared to dosage error data residing in a dosage error database. As described above with reference to FIG. 2, the submitted drug product and submitted drug strength may be compared to dosage error pair data to determine if the combination is a member of a dosage error pair. The processing of block 306 may be made by interrogating the dosage error database based on the submitted drug product. The dosage error database may include one or more data tables populated with any or all available dosage error pairs. In certain embodiments, each entry in a dosage error pair table may indicate whether the drug pair is active or inactive, permitting active dosage error pairs to be searched, while ignoring inactive drug pairs. Similarly, as described above, one or more dosage error pairs may be weighted to facilitate deciding whether an edit action and/or message should be performed. A pharmacy manager, service provider, or other system administrator may be provided with the ability to define whether a dosage error pair is to be active or inactive, and/or control the respective weighting, and may thus be able to control which dosage drug pairs are to be included and how much value should be attributed when performing the dosage verification processing. Other embodiments, however, may not distinguish between active and inactive dosage error pairs, such that all drug pairs in the database would be active and searched.

Following block 306 is block 308, in which the submitted drug product and submitted drug strength may be compared to patient history data for the patient to whom the prescription transaction relates. As described above with reference to FIG. 2, the dosage verification module may compare the submitted drug product and strength combination to previous prescription transactions and/or previous prescriptions filled for the patient. Thus, knowing that the patient has been previously prescribed the submitted drug and strength combination may aid in determining that the combination is valid and does not include any dosage errors, under the premise that a second or additional prescription for the same combination is unlikely to be an error.

In another embodiment, the dosage verification module may compare the counterpart drug and strength combination identified in the dosage error pairs, such as may be identified at block 306, with the patient history data to determine whether the counterpart strength has been prescribed for the submitted drug product has been prescribed to the patient. Thus, patient history data indicating that a counterpart strength has been previously prescribed may indicate a higher likelihood of a dosage error.

In one embodiment, the dosage verification module may include a duration limitation, which may be set by a pharmacy manager, service provider, or other system administrator, to limit the duration of the patient's past prescription transactions that are reviewed in this comparison. For example, the duration limitation may be set to 100 days (or any other duration), such that only prescription data for the patient in the past 100 days is reviewed when performing the comparison.

In some example embodiments, the patient history comparison results may be dispositive, such that if the submitted drug and strength combination was previously prescribed for the patient, then the combination is assumed correct and typical processing may continue. Though, in other embodiments, the patient history comparisons may be only one of many comparisons performed when verifying the submitted dosages.

As illustrated in FIG. 3, in example embodiments, the dosage verification processing of the method 300 may include only dosage error pair processing and not patient history processing; while in other example embodiments, only patient history processing and not dosage error pair processing may be performed. Though, as described above, in one embodiment, both are performed, or both may optionally be performed such as if certain determinations by one of the steps may be dispositive, obviating the need to perform the other step. For example, if it is determined that the submitted drug strength is not a member of a dosage error pair, then some methods may halt dosage verification processing at that point and continue typical processing of the prescription transaction. Similarly, some methods may first perform patient history processing, and if the submitted drug and strength combination was previously prescribed (or if the prescription transaction was for a refill), then the dosage verification may be halted and typical prescription transaction processing may continue.

Following block 308 is block 310, in which the dosage verification module may optionally perform additional dosage verification processing. As described in more detail herein, additional dosage verification processing may include, but is not limited to, maximum dosage processing and/or minimum dosage processing (also collectively referred to herein as "absolute dosage processing"), typical dosage processing, and additional patient data processing. For example, if either or both of the dosage error pair comparison performed in block 306 or the patient history comparison performed in block 308 indicate that the submitted strength may be incorrect, the dosage verification module can perform one or more additional dosage processing steps to arrive at a more reliable determination as to whether to perform an edit action and/or message the pharmacy.

Following block 310 is decision block 312, in which a determination may be made as to whether the submitted drug strength (or any other dosage-related data) is incorrect. This determination may be made based at least in part on the one or more dosage verification processing steps performed, such as in blocks 306, 308, 310. In example embodiments, any single factor may cause an edit action to be performed; though, in other embodiments, a predetermined combination of factors may cause an edit action to be performed (e.g., both a member of a dosage error pair and not in the patient's prescription history data).

The combinations of factors, weighting, or other guidance used in making the determination whether to perform an edit action can be adjustable, such as by a pharmacy manager, service provider, payer, or other system administrator. Providing flexibility and customization allows participating entities to adapt the sensitivity of the dosage verification module and associated processing, depending upon their individual needs. For example, certain pharmacies may prefer to receive a greater number of messages requesting verification of dosage strengths, while others may prefer to limit the number of messages and only want to see messages for those strengths having a high likelihood of error, which may reduce the likelihood of false positives, but may also increase the possibility of filling an incorrect strength. Moreover, in example embodiments, the dosage verification module can be adjusted to permit participating entities to predetermine certain drug and strength combinations and/or identify specialized messages for automatic transmission when a prescription transaction includes matching data, such as when certain combinations are extremely dangerous, expensive, or very rarely prescribed, for example. In other embodiments, a participating entity may individually determine which types of dosage verification processing are to be performed by choosing one or more of the dosage error pair processing, patient history processing, maximum/minimum dosage processing, typical dosage processing, and the like. In various embodiments, the sensitivity may be adjusted on an entity level, such that each entity (e.g., pharmacy or payer) may determine system and messaging sensitivity, at the service provider level, such that any prescription transaction processed by a given service provider is processed at the same level of sensitivity, or by any other criteria, such as time of day, geography, prescriber, day of week, time of year, and the like.

Accordingly, permitting various levels of customization and flexibility may reduce what some may perceive as "noise" in the system, thereby increasing the reliance on the messaging, which may ultimately provide much more efficient prescription transaction and/or claims processing for all participating entities, and potentially avoid disbursement of unintended medication.

With continued reference to FIG. 3, if it is determined at block 312 that the submitted strength in the prescription transaction is not incorrect, then block 314 follows, in which typical prescription transaction processing may continue 314.

However, if it is determined at block 312 that the submitted drug strength may be incorrect, then block 316 follows in which one or more edit actions may be performed. Edit actions may include, but are not limited to, generating and transmitting an error message, generating and transmitting a warning message, generating and transmitting a verification inquiry, generating and transmitting a rejection message, storing prescription data and associated determinations for subsequent analysis and reporting, or taking no action. Messaging resulting from edit actions may include one or more of these message types and notifications, such as a prescription rejection and an error message, which may effectively reject the submitted prescription transaction but also inform the pharmacy as to the reason for rejection. Edit action parameters may be set to determine what type of edit actions to pursue in given situations. Edit action parameters, may include identifying which type of dosage verification processing to perform and/or review, weighting to associated factors (e.g., dosage error pairs, weighting processing steps, etc.), pharmacy overrides, and the like. In accordance with certain embodiments, edit action parameters may be configurable by the pharmacy manager, service provider, payer, or other system administrator.

For example, in one embodiment, edit action parameters may be used to define the situations in which a prescription transaction should be rejected, the situations in which prescription transactions should be recorded for later analysis and reporting, and the situations in which no action should be taken. In certain embodiments, under most cases, all rejected prescription transactions will likely be recorded; however, some transactions may be recorded even if they are not rejected. For example, a prescription transaction may violate certain dosage verification criteria, but for some reason (e.g., transaction relates to a refill prescription or is the same as a previous transaction in the patient's history data) the transaction may not be rejected. Such a prescription transaction may still be recoded for later analysis and reporting. As a result of the edit action parameters, indicators may be set for each prescription transaction as it is processed via the various dosage verification processing steps described herein. The combination of indicators set will aid in determining which edit action to perform.

The method 300 may end after block 316, in which a received prescription transaction has been processed by the dosage verification module, determining whether the submitted dosage information may have an incorrect entry, and performing the appropriate edit action or continuing processing of the prescription transaction.

Figure 4A:
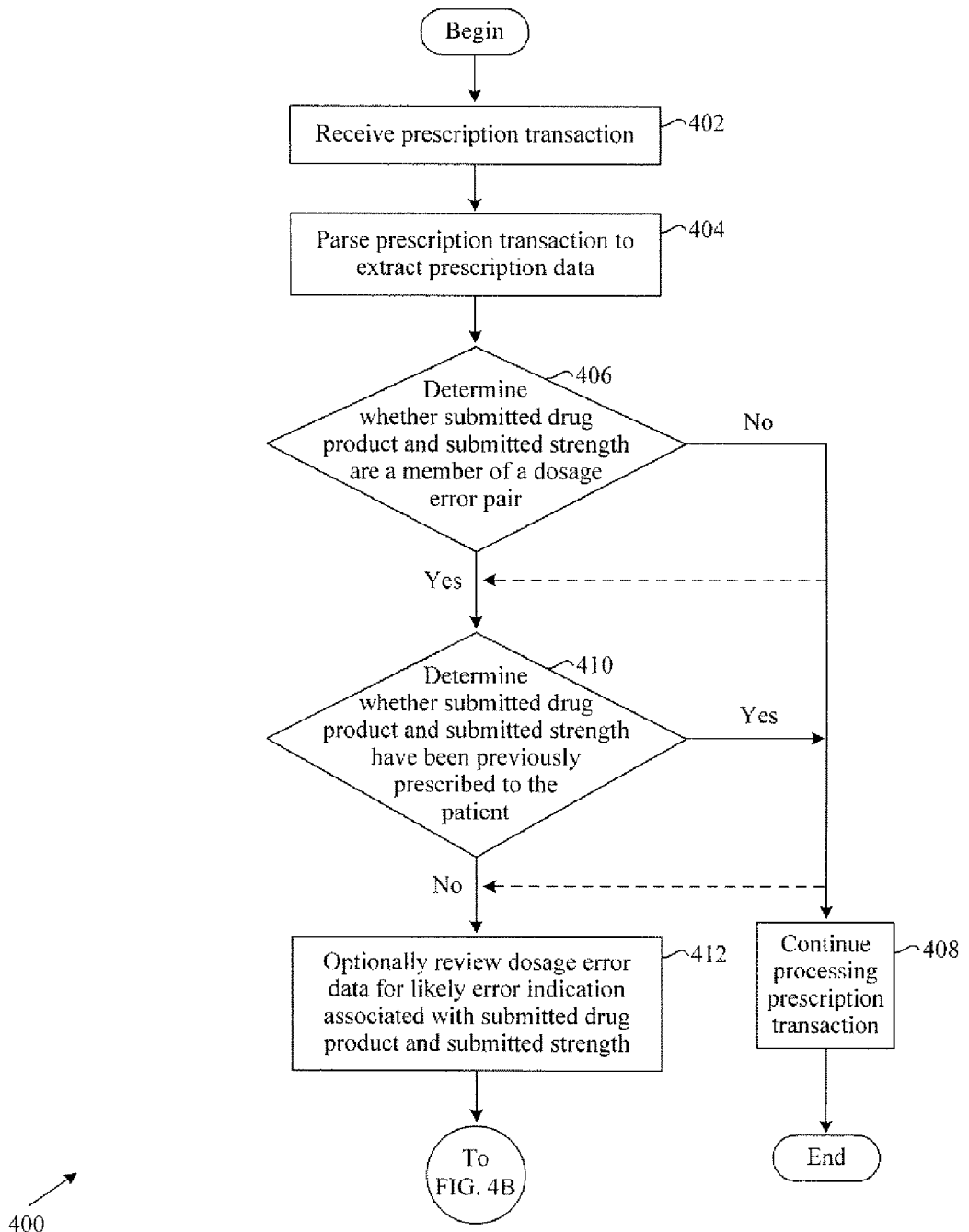
FIGS. 4A and 4B illustrate an example detailed flow diagram for performing dosage verification processing on a prescription transaction, according to one example embodiment.
Figure 4B:
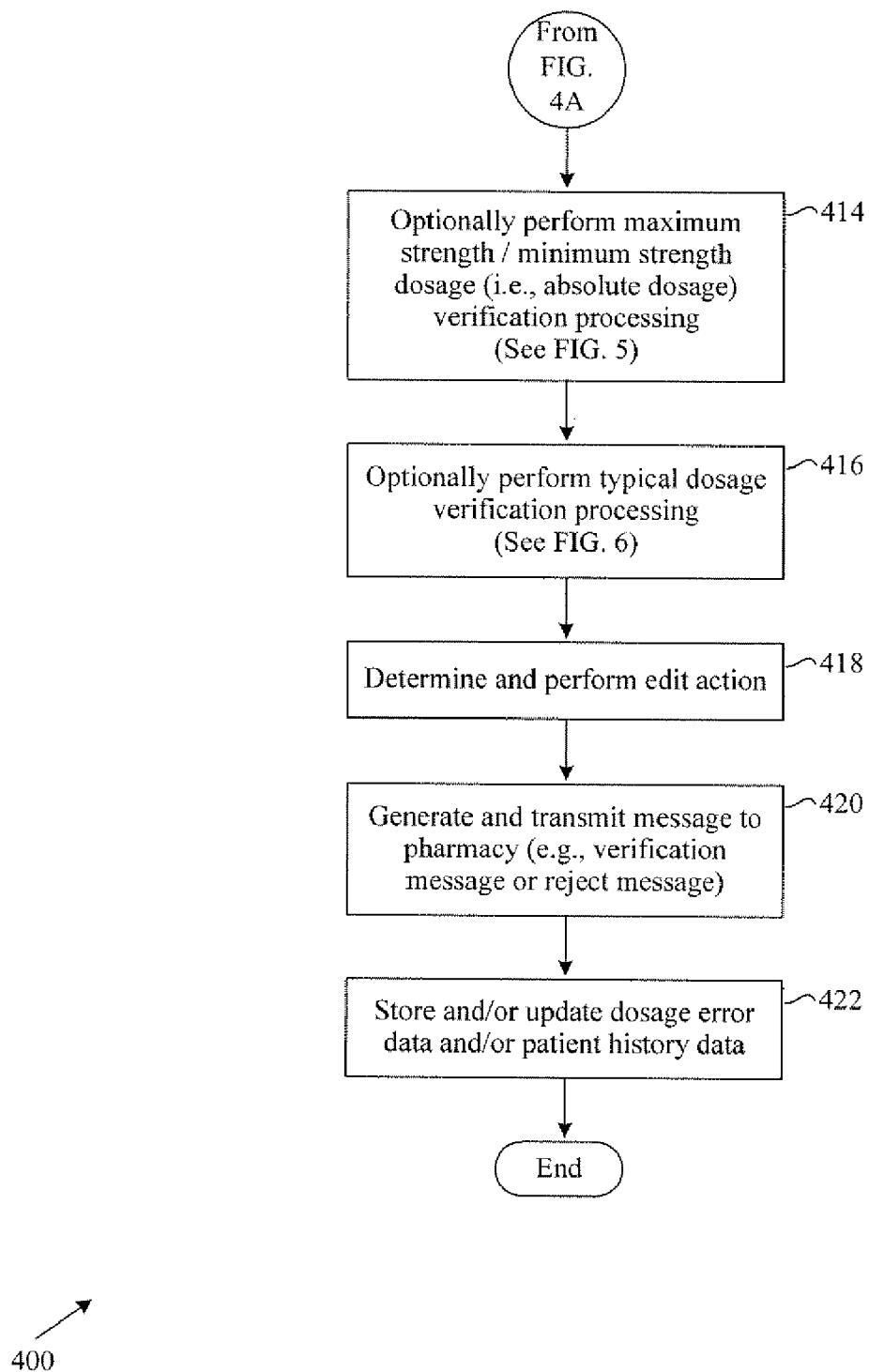

FIGS. 4A and 4B illustrate flow diagrams of an example method 400 for performing dosage verification processing on a prescription transaction, according to one example embodiment. This example method 400 illustrates in more detail the additional processing steps that may be performed when conducting dosage verification processing, such as may be performed by a service provider 104 and an associated dosage verification module 108 as described with reference with FIGS. 1-2.

The method 400 begins at block 402. At block 402, a service provider may receive a prescription transaction in a manner similar to that described with reference to FIG. 3. Following block 402 is block 404, in which the prescription transaction may be parsed to extract prescription data from the transaction.

Following block 404 is decision block 406, in which it may be determined if the submitted drug product and the submitted strength are members of a dosage error pair stored in a dosage error database. In an illustrative example, the prescription transaction may identify the submitted drug product and submitted strength as "Clozaril" and "25 mg," respectively. In one case, the dosage verification module may perform a database lookup on the dosage error pair data based on "Clozaril" and identify that a dosage error pair exists for Clozaril "Clozaril 12.5 mg" and "Clozaril 25 mg." Because a dosage error pair exists, there may be a potential that the submitted strength of "25 mg" is incorrect, and that the Clozaril counterpart at "12.5 mg" may be the intended prescription. According to one embodiment, the mere existence of the submitted drug product in the dosage error pair data may indicate a likelihood of error; though, in other embodiments, a likelihood of error may only be determined if both the drug product and the strength are in the dosage error pair data. Thus, additional dosage verification processing may be performed to further determine the likelihood that the submitted strength is incorrect. In yet other embodiments, the simple fact that the submitted drug product and strength combination has an alternative strength may be sufficient cause to perform an edit action. As a result of the dosage error pair processing in block 406, a dosage error pair indicator may be set if it is determined that a potential error exists.

In example embodiments, while performing dosage error pair processing at block 406, the dosage verification module may retrieve and store data from the dosage error database for subsequent use, such as to provide additional detail in messages transmitted to the pharmacy or to store for subsequent analysis and reporting. For example, the counterpart strength may be captured and later provided to the pharmacy when requesting verification of a potentially incorrect strength. This counterpart strength may also be referred to interchangeably herein as a "suggested strength."

However, if it is determined at block 406 that the submitted drug product is not a member of the dosage error pair data, and thus does not have another potential submitted strength counterpart, then the method may continue to block 408 in which the service provider may continue typical prescription transaction processing. In this ease, no dosage error pair indicator would be set. Though, in one embodiment, as illustrated as optionally occurring in FIGS. 4A and 4B, even if it is determined at block 406 that the submitted drug product is not a member of the dosage error pair data, block 410 may follow in which additional dosage verification processing may be performed.

In decision block 410, additional dosage verification processing of the submitted drug product and/or strength may continue. At decision block 410, it may be deter ruined whether the submitted drug product and submitted strength combination has been previously prescribed for the patient. As described in detail with reference to FIG. 2A, the service provider may include a patient history database including data representing some or all of the patient's previous prescription transactions. In embodiments in which the patient history processing is performed, the dosage verification module may extract a patient identifier from the prescription transaction and access prescription history information for that patient. In one example, the dosage verification module may perform a lookup on the submitted drug product and strength combination, such as by searching the NDC#, the drug product name, the drug product name and strength, etc., to determine whether the combination has been previously prescribed for the patient. For example, if the "Clozaril" has been prescribed, but only in the "12.5 mg" strength, then the dosage verification module may indicate that there exists a likelihood that the "25 mg" strength is an error and set a patient history indicator. Conversely, if the dosage verification module determines from the patient history database that "25 mg" strength has been previously prescribed, then the module may indicate that the submitted strength is likely a valid submitted strength and not set the patient history indicator.

In example embodiments, while performing patient history processing at block 410, the dosage verification module may retrieve and store data from the patient history database for subsequent use, such as to provide additional detail in messages transmitted to the pharmacy or to store for subsequent analysis and reporting. For example, the dosage verification module may transmit the previously prescribed strength and optionally date information to the pharmacy as a suggested strength when messaging the pharmacy to request verification.

In addition to comparing the submitted drug and strength combination, the dosage verification module may perform additional processing using information stored in the patient history database. For example, in one embodiment, additional dosage verification processing may compare the submitted strength with accepted information and/or guidelines about the submitted drug, such as comparing the dosage with typical or accepted dosages for patients having similar weights or patients of similar ages. In other example embodiments, other patient information may also be used to perform additional dosage verification processing.

In one embodiment, the dosage verification module may use information stored in the patient history database to determine if the prescription is for a refill in a similar manner as when conducting the other prescription transaction history processing. Though, in other embodiments, whether the prescription is a refill can be extracted from the prescription transaction information. Like the patient history processing, if the dosage verification module determines that the prescription transaction is for a refill, then it may indicate that the dosage information is assumed correct, and no further dosage verification processing needs to occur. Though, in other embodiments, whether the prescription transaction is for a refill may simply be performed as one of multiple processing steps. Moreover, determining whether the prescription transaction was for a refill may be performed at any point along the processing—for example, in one embodiment it may be the initial inquiry, upon which additional processing may not be necessary.

If it is determined at block 410 that the submitted drug product and strength combination has been previously prescribed to the patient, and thus is likely correct, the method may continue to block 408 in which the service provider may continue typical prescription transaction processing. Though, in one embodiment, as illustrated as optionally occurring in FIGS. 4A and 4B, even if it is determined at block 410 that the submitted drug product has been previously prescribed for the patient, block 412 may follow in which additional dosage verification processing may be performed. For example, some entities may want to always perform maximum and minimum dosage processing or typical dosage processing.

Following block 410 is optional block 412, in which additional dosage error data may be reviewed to determine if the submitted drug strength is likely an incorrect strength. As described above with reference to FIG. 2A, the dosage error database may include information in addition to the dosage error pair data. For example, data may indicate drug and strength combinations which are deemed as highly likely to be an error, such as, drug and strength combinations that are not commercially available or very rarely prescribed (error strengths). Thus, if a prescription transaction includes a drug and strength combination indicated as highly likely to be an error, the dosage verification module may determine that the submitted strength is likely incorrect and an indicator may be set. In yet another example, at block 412 weighting associated with the dosage error data may be considered by the dosage verification module to aid in determining the likelihood of an incorrect strength. Any other data stored in the drug error database or otherwise associated with the dosage verification module may be considered at block 412 in various embodiments.

Following block 412 is optional block 414, in which minimum and maximum dosage processing (also collectively referred to "absolute dosage processing") may optionally be performed. Absolute dosage processing can be performed in order to determine whether the submitted daily dosage meets the maximum dosing criteria and the minimum dosing criteria for the submitted drug product, as described with reference to FIG. 5 and in more detail in commonly owned U.S. patent application Ser. No. 10/339,230 entitled "Systems and Methods for Look-Alike Sound-Alike Medication Error Messaging," which is incorporated by reference herein in its entirety.

In one example embodiment, if the submitted daily dosage is greater than the recommended maximum daily dosage for that drug product (optionally considering other factors, such as age, weight, sex, etc.) and/or less than the recommended minimum daily dosage, then the dosage verification module may indicate the submitted strength is highly likely to be incorrect and an absolute dosage indicator may be set. Like the other dosage verification processing steps, additional data can be collected and stored for subsequent use, such as to include in a message or store for later reporting or analysis. As used herein, the term "submitted daily dosage" generally refers to the prescribed dosage to be taken in one day, and can be actually provided expressly in prescription transaction data or may be calculated from other prescription transaction data, such as calculating it from the quantity dispensed and days supply data. Accordingly, the term "submitted daily dosage" is not intended to be limited to values expressly provided in prescription transaction data and can be derived therefrom.

Following block 414 is optional block 416, in which typical dosage processing may optionally be performed. Typical dosage processing can be performed in order to determine whether the submitted daily dosage is at or near statistically-determined daily dosages for the respective drug product. For example, while performing typical dosage processing, the dosage verification module may determine whether the submitted daily dosages are at or near common daily dosages, most common daily dosages, or determine the degree of variance from these or any other statistically-determined dosage trends, as described with reference to FIG. 6 and in more detail in commonly owned U.S. patent application Ser. No. 10/339,230 entitled "Systems and Methods for Look-Alike Sound-Alike Medication Error Messaging."

In one example embodiment, if the submitted daily dosage is not the same or within an acceptable degree of variance from a statistically-determined typical dosage, then the dosage verification module may indicate the submitted strength is highly likely to be incorrect and a typical dosage indicator may be set. Like the other dosage verification processing steps, additional data can be collected and stored for subsequent use, such as to include in a message or store for later reporting or analysis.

After performing one or more of the above-described dosage verification processing steps, the method may continue to block 418, in which the dosage verification module may determine whether any edit actions are to be performed, and if so, which. The dosage verification module may analyze the results of the dosage verification processing to determine whether an edit action is to be performed. For example, in one embodiment in which multiple dosage verification processing steps are performed indicators or flags may be set at each processing step depending upon the determination made. Any combinations of indicators may dictate whether an edit action should be performed, as may be configured by the service provider, or by another entity, such as a pharmacy, healthcare provider, or payer, for example. As previously described, the edit actions may be to generate and transmit one or more messages, generate and transmit a transaction rejection, store data for subsequent analysis or reporting, or to do nothing.

Edit actions other than messages, rejections, and storage steps are possible in certain embodiments. For example, an edit action may be defined to set a given indicator that a message should be sent to the pharmacist as an information message when the prescription transaction is not rejected. In another example, an edit action may be defined to set an indicator that a message should be printed on a warning label of the dispensed packaging. These and other examples of edit actions are contemplated in connection with any or all verification processes described herein.

Indicators, associated edit actions, and corresponding messages, for example, may be stored in one or more lookup tables or other suitable data tables within a database accessible by the service provider (or any other entity). Table II below illustrates example indicator conditions, and possible resulting edit actions, according to one embodiment.

TABLE II

Example Indicator Conditions and Associated Edit Actions

| In Pair Flag | Not In Pt. History Flag | Max/ Min Violation Flag | Typical Violation Flag | Edit Action | Message |
|---|---|---|---|---|---|
| Y | Y | Y | Y | Message = Yes Store Data = Yes | Above Max of [x]/ Below Min of [y]; Atypical Dose; Possible Alternate Strength of [x]; Pt. History of [y]; Please Verify Dose and Strength |
| N | Y | Y | Y | Message = Yes Store Data = Yes | Above Max of [x]/Below Min of [y]; Atypical Dose; Pt. History of [y]; Please Verify Dose and Strength |
| Y | N | Y | Y | Message = Yes Store Data = Yes | Above Max of [x]/ Below Min of [y]; Atypical Dose; Possible Alternate Strength of [x]; Please Verify Dose and Strength |
| Y | Y | N | Y | Message = Yes Store Data = Yes | Atypical Dose; Possible Alternate Strength of [x]; Pt. History of [y]; Please Verify Dose and Strength |
| N | N | Y | Y | Message = Yes Store Data = Yes | Above Max of [x]/ Below Min of [y]; Atypical Dose; Please Verify Dose and Strength |
| N | Y | N | Y | Message = Yes Store Data = Yes | Atypical Dose; Pt. History of [y]; Please Verify Dose and Strength |
| Y | N | N | Y | Message = Yes Store Data = Yes | Atypical Dose; Possible Alternate Strength of [x]; Please Verify Dose and Strength |
| Y | Y | N | N | Message = No Store Data = Yes | |
| N | N | N | Y | Message = No Store Data = Yes | |
| N | Y | N | N | Message = No Store Data = Yes | |
| Y | N | N | N | Message = No | |
| N | N | N | N | Message = No | |
| ... | ... | ... | ... | ... | ... |

Accordingly, as is illustrated in Table II by example, various indicator combinations could result from the verification processing steps illustrated by method 400, and an example message may be generated and transmitted to the pharmacy. For example, the first case illustrates a scenario in which all processing steps raised a question as to whether the submitted drug strength is correct or not, thus indicators set for each step. For this example case, the edit action is set to generate a message and store data. As an example, "Clozaril 25 mg" may be submitted on the prescription transaction with a quantity of four tablets per day, which would result in a calculated daily dosage of 100 mg; although, the intended prescription was for four 12.5 mg tablets a day for a daily dosage of 50 mg. According to this example, the dosage verification module would identify that a dosage error pair exists in the dosage error database. The first case of Table II also sets the patient history indicator because the patient for this example has not previously been prescribed a 25 mg strength of Clozaril (and the prescription is not for a refill). Also, the indicators for both the absolute dosage processing and the typical dosage processing are set because the calculated daily dosage of 100 mg of Clozaril may exceed the maximum recommended daily dosage and thus would also not be a statistically-determined typical daily dosage.

Accordingly, in this first case example, the dosage verification module would determine that an indicator combination such as this (all indicator flags set) suggests that both a message be generated and transmitted and the transaction data be stored for subsequent analysis and/or reporting. An example of a message format for this case is displayed in the last column of Table II, and in this example may read: "Above Max of 50 mg; Atypical Dose; Possible Alternate Strength of 12.5 mg; Pt. History of 12.5 mg; Please Verify Dose and Strength." The additional data that may be inserted into the messages, such as the patient history or the suggested strengths, may be obtained and stored during the dosage verification processing in blocks 406, 410, 412, 414, 416, or may be retrieved from one or more databases while generating the message prior to transmission.

Table II and the corresponding discussion is provided for illustrative purposes only, and is not intended to be limited. Moreover, the cases illustrated in Table II are not intended to be a complete listing of the possible combinations, are not intended to represent required outcomes, and some cases listed may never occur.

Following block 418 is block 420, in which one or more messages may be generated and transmitted to the pharmacy (or any other entity), if the edit action parameters so indicate. As illustrated in the message examples of Table II, if more than one of the verification processing steps indicate an incorrect strength is likely, messages may include multiple reasons and data extracted during or as a result of the respective verification processing steps for which an indicator is set. However, inclusion of multiple messages in a message may be redundant or otherwise unnecessary. Therefore, if the prescription transaction is to be rejected and/or a message sent based on the results of multiple verification processes, logic may be employed to prioritize and select the message or messages to be included, according to one embodiment. In example embodiments, any of the participating entities may customize or otherwise control the generation, content, and transmission of messages as desired.

Edit actions are referred to as being administratively-defined in example embodiments because a system administrator, such as a pharmacy manager or a service provider, may determine which edit action is applicable to a given situation. As an example, for various reasons one system administrator may determine that a reject message is appropriate when a prescription transaction relates to a refill with lower than the absolute minimum daily dosage, while another system administrator may determine that a store data edit action is appropriate for the same situation. In certain embodiments, edit actions for given situations may be re-set at any time by one or more participating entities. For example, if it is determined that a particular verification message or reject message for a particular situation yields too may "false positive" messages, the edit action and associated indicators for that situation may be changed, such as to store data or no action. As used herein, the term "false positive" generally refers to edit actions that are taken (e.g., verification or warning message) for a submitted drug product and strength combination that was in fact the intended combination.

In example embodiments, messages may be transmitted in real-time or near real-time. Though, in other example embodiments, messages may be periodically transmitted, such as part of a batch process. As described and illustrated herein, in one embodiment the messages may be transmitted to the pharmacy from which the prescription transaction was received. Though, in other embodiments, messages may be sent to an associated physician or other healthcare provider (who's information may be extracted from the prescription transaction), such as may be done to aid in correcting administrative and prescription entering procedures. In yet other embodiments, messages may be transmitted to the associated payer (also extracted from the prescription transaction), such as may be done to facilitate their performance reporting and tracking of pharmacies, healthcare providers, and the like.

Following block 420 is block 422, in which selected messages, prescription transaction data, and/or patient data is recorded, if appropriate, for subsequent reporting and analysis. Again, whether or not recording of prescription transaction data is appropriate may be conditioned on the edit action parameters or indicators that were generated during respective dosage verification processes. In one embodiment, if at least one indicator suggests that the submitted strength (or other data) is potentially incorrect, prescription transaction data, patient data, and/or appropriate message(s) can be recorded. In addition, if at least one indicator suggests that the prescription claim should be captured (i.e., recorded but no message generated), such action should be taken. If no indicators suggest that an action should be taken for the prescription claim, then no data is recorded in some embodiments. In example embodiments, various edit action parameters may also dictate which prescription transaction data is to be recorded. For example, different data may need to be recorded for reporting and analysis of non-compliance with typical dosing criteria or absolute dosing criteria than may be recorded when a dosage error pair indicator is set.

Figure 7:
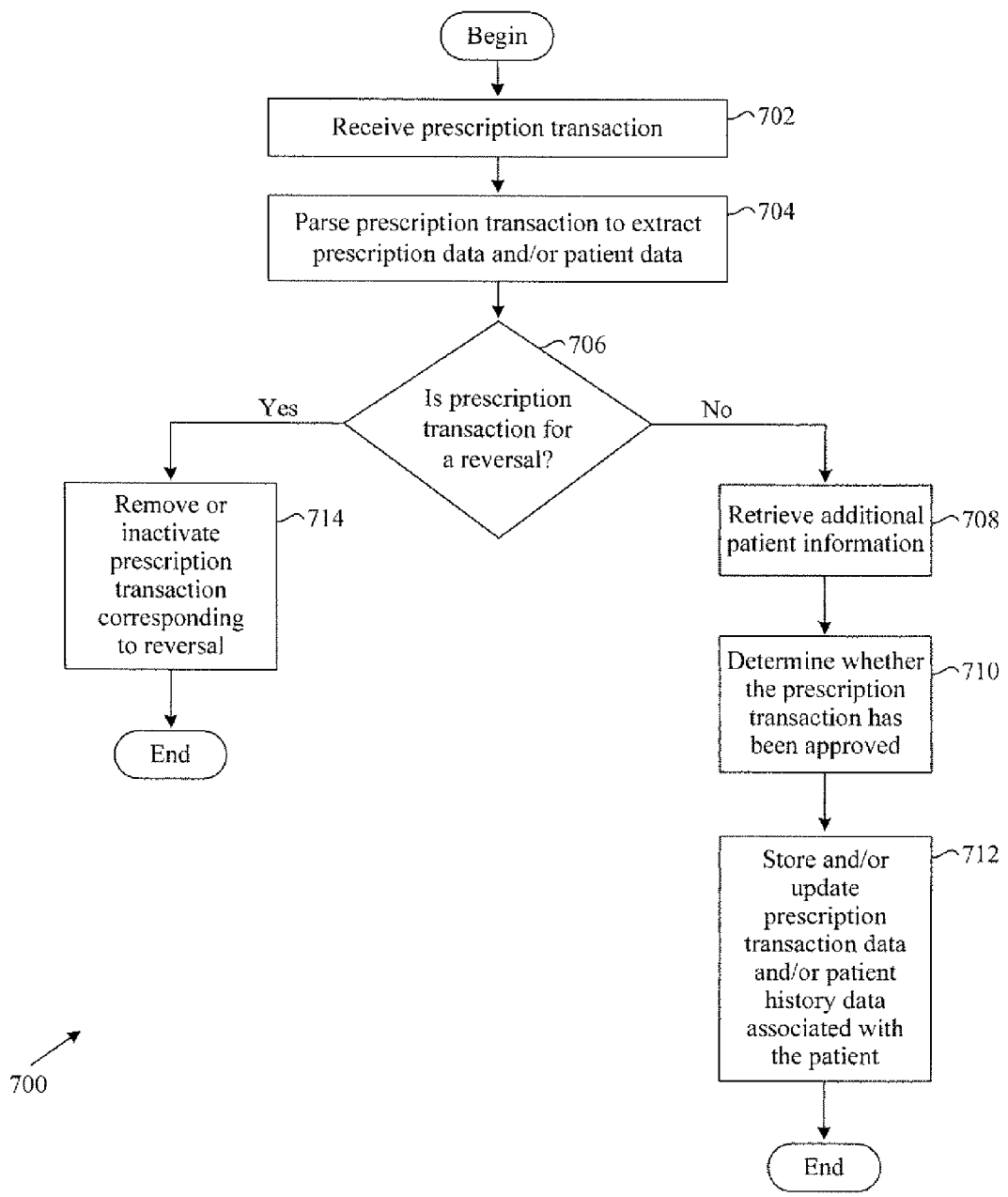
FIG. 7 illustrates an example flow diagram for maintaining a patient history database, according to an example embodiment of the invention.

Moreover, in example embodiments in which a patient history database is being built, then all prescription transaction data can be recorded, and subsequently updated upon determining a valid prescription transaction with correct drug combination and strengths have been submitted. In other example embodiments, the patient history database may be updated at another point during prescription processing, such as after receiving approval messages from a payer for the prescription claim, upon transmitting approval to the pharmacy for dispensing, or upon receiving an indication from a pharmacy that the drug has been dispensed for the patient. FIG. 7 and the accompanying description provides additional detail regarding example embodiments that include building a patient history database.

In addition, in example embodiments, dosage verification processing results and/or prescription transaction data may be stored to facilitate updating one or more databases accessed by the dosage verification module and/or verification logic. Thus, according to one example embodiment, the dosage verification module may gain intelligence or otherwise "learn" during dosage verification processing, updating the associated logic, rules, algorithms, edit action parameters, and/or data in response to the outcomes of particular dosage verification processing actions. For example, upon identifying potential errors, the dosage verification module may track the occurrence of likely errors for a given drug product and strength combination, which may be used to weight or otherwise indicate more likely or less likely error prone combinations. In another example, after messaging a pharmacy of a potential error and upon receiving a verification indicating that the originally submitted drug product and strength combination were correct or incorrect, the dosage error database or other databases may be updated, such as to add dosage error pair data or to indicate more likely or less likely error prone combinations. Similar responses may also serve to provide additional data and statistical measures for other processing that may optionally be performed, such as the typical dosage processing.

In addition, data stored by the service provider may be analyzed by the service provider, such as may be done to update its dosage verification system, track pharmacy and/or healthcare provider performance, provide metrics to payers, and the like. In example embodiments, the stored data may dissected and grouped for further analysis, such as analyzing at the pharmacy chain level, pharmacy store level, physician level, patient demographic level, and the like, in order to form more specific conclusions regarding drug dosage errors. In other embodiments, some or all of the stored data may be provided to the other participating entities for their individual analyses.

Although not illustrated in FIG. 3 or 4, it will be appreciated that in certain embodiments, the system may be configured to accept "overrides" from pharmacists or system administrators. In other words, a pharmacist or system administrator may be able to override a rejection of a prescription transaction and cause the prescription transaction to be processed. In one embodiment, the pharmacists or system administrator may need to provide a code or some other identifier that indicates his/her authority to request the override. In another embodiment, the pharmacist may need to change some portion of the prescription transaction data in order to request an override. In certain embodiments, if an override is submitted, any messages previously produced by the dosage verification processing may be attached to one or more post-edit messages delivered to the pharmacist.

Edit overrides and transactions resulting therefrom may also be recorded for subsequent reporting and analysis. Comparison of all versions of a particular prescription transaction through a process known as "prescription matching" can provide useful insight into the reason(s) why the pharmacist (or other entity) may have made an error or why the reject message was a false positive if the pharmacist in fact did enter the correct strength. Prescription matching can involve identifying all prescription transactions (including claims and/or reversals) having the same date of service and prescription number from the same pharmacy. The latest such prescription transaction is designated as the "matching prescription" and is given a key to link it back to prior version(s) of the transaction that invoked the reject message.

The method 400 may end after block 422, in which a received prescription transaction has been processed by the dosage verification module, determining whether the submitted dosage information may have an incorrect entry, and performing the appropriate edit action or continuing processing of the prescription transaction.

Figure 5:
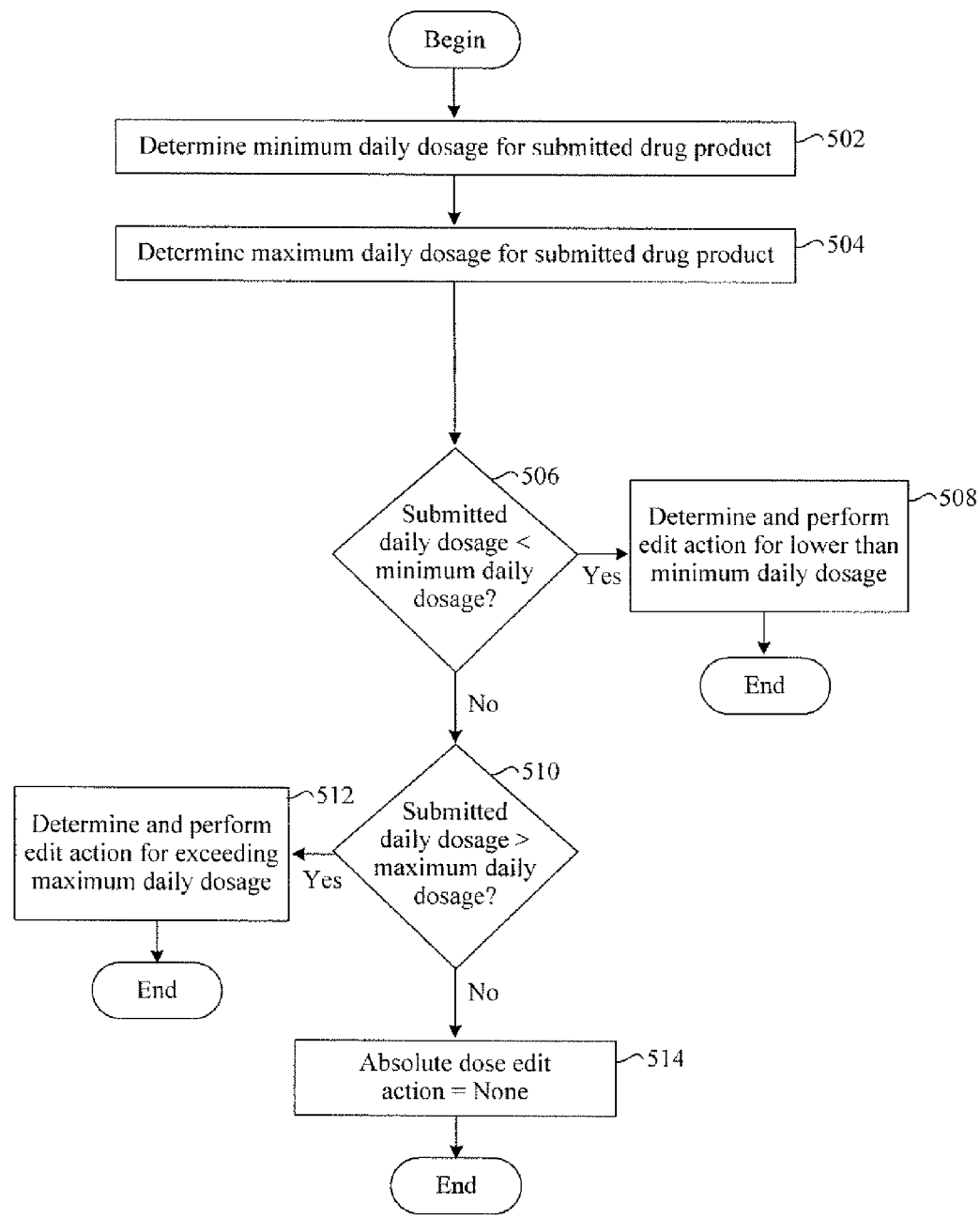
FIG. 5 illustrates an example flow diagram for performing prescription verification processing that includes absolute dosage processing, according to an example embodiment of the invention.

FIG. 5 is a flowchart illustrating an example method 500 for performing absolute dosage processing, according to one example embodiment. As described with reference to FIGS. 4A and 4B, a service provider and associated dosage verification module, such as the service provider 104 and dosage verification module 108 as described with reference to FIGS. 1 and 2, may optionally perform absolute dosage processing on prescription transaction data as part of an overall dosage verification process. The commonly owned U.S. patent application Ser. No. 10/339,230 entitled "Systems and Methods for Look-Alike Sound-Alike Medication Error Messaging" also provides additional detail regarding absolute dosage processing, any of which may be included in the overall dosage verification processing described herein.

The method 500 begins at block 502, where the absolute minimum daily dosage for the submitted drug product may be determined. The absolute minimum daily dosage may be determined by interrogating a database storing such information. Absolute minimum daily dosages can be defined by various text references known in the healthcare industry, such as the Physicians Desk Reference ("PDR"), the United States Pharmacopedia Dispensing Information ("USPDI"), and the like, as well as by the FDA.

Following block 502 is block 504, in which the absolute maximum daily dosage for the submitted drug product can be determined. Again, information regarding maximum daily dosages for drug products may be stored in and retrieved from a database in a manner similar to the absolute minimum daily dosages.

At block 506, it is determined whether the submitted daily dosage, which can be calculated from quantity dispensed and days supply data or provided expressly, is less than the absolute minimum daily dosage for the submitted drug product. If so, the method moves to block 508 to determine an edit action, or otherwise set an indicator, for a submitted strength that is lower than the absolute minimum daily dosage for the submitted drug product.

After determining the desired edit action and/or setting the appropriate indicator at block 508, the method 500 may end. Upon completing the method 500, the dosage verification module may perform additional dosage verification processing, such as may be indicated after block 414 of FIG. 4B, for example.

Returning to block 506, if it is determined that the submitted doses per day is not less than the absolute minimum doses per day for the submitted drug product, the method may proceed to block 510 to determine whether the submitted daily dosage is greater than the absolute maximum daily dosage for the submitted drug product. If the submitted daily dosage is greater than the absolute maximum daily dosage for the submitted drug product, the method may proceed to block 512 to determine an edit action, or otherwise set an indicator, for a submitted strength exceeding the absolute maximum daily dosage for the submitted drug product.

After determining a suitable edit action at either block 508 or 512, the method 500 may end and/or optionally perform additional dosage verification processing, such as may be indicated after block 414 of FIG. 4B, for example.

If at block 510 it is determined that the submitted doses per day is not greater than the absolute maximum daily dosage for the submitted drug product, the submitted daily dosage can be determined to satisfy the absolute dosing criteria for the submitted drug product. In that case, the method may proceed to block 514 where no indicator is set, and thus no corresponding edit action would be processed.

The method 500 may end after block 514 and/or optionally perform additional dosage verification processing, such as may be indicated after block 414 of FIG. 4B.

Figure 6:
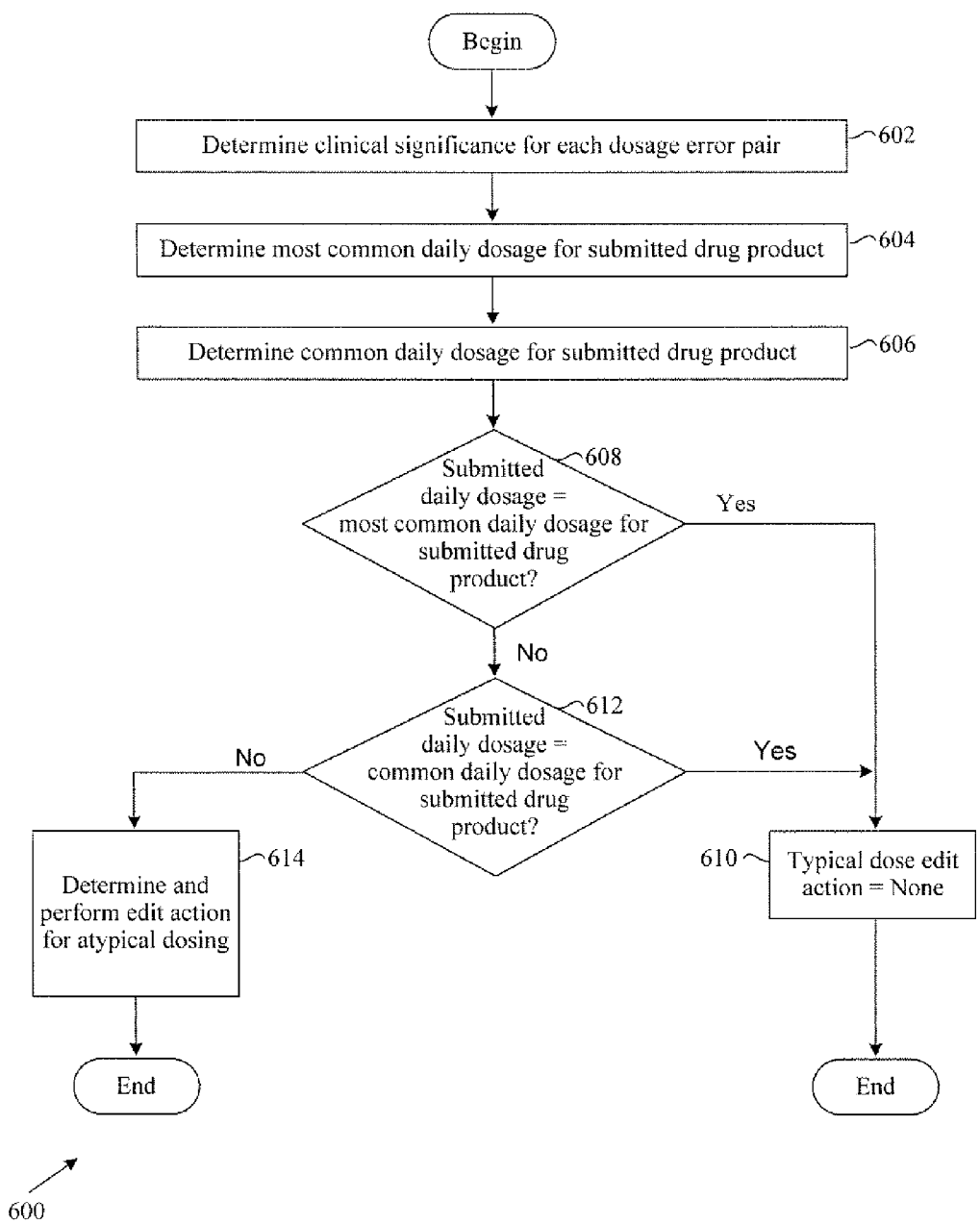
FIG. 6 illustrates an example flow diagram for performing prescription verification processing that includes typical dosage processing, according to an example embodiment of the invention.

FIG. 6 is a flowchart illustrating an example method 600 for performing typical dosage processing, according to one example embodiment. As described with reference to FIG. 4B, a service provider and associated dosage verification module, such as the service provider 104 and dosage verification module 108 as described with reference to FIGS. 1 and 2, may optionally perform typical dosage processing on prescription transaction data using statistically-determined typical dosage data as part of an overall dosage verification process. The commonly owned U.S. patent application Ser. No. 10/339,230 entitled "Systems and Methods for Look-Alike Sound-Alike Medication Error Messaging" also provides additional detail regarding typical dosage processing, any of which may be included in the overall dosage verification processing described herein.

The method 600 may begin at optional block 602. According to one embodiment, if the dosage verification module identifies one or more dosage error pairs associated with the submitted drug product and submitted strength combination, the clinical significance for a dosage error pair is optionally determined at block 602.

Clinical significance values may be stored in a database in association with corresponding dosage error pairs and may be modified as appropriate. Clinical significance may be represented by a clinically-determined value assigned to a dosage error pair, and used to quantify the consequences of a drug strength error caused by substituting one drug strength of the submitted drug product with the counterpart strength in the dosage error pair. As an illustrative example, a clinical significance of 1 may be used to indicate that a dosage error with the counterpart strength could be harmful or fatal; a clinical significance of 2 may be used to indicate that a dosage error could have a mild effect on the patient; and a clinical significance of 3 may be used to indicate that a dosage error could have little or no effect on the patient. Clinical significance values may be determined in numerous manners, and may be derived from clinical data, knowledge, and/or expertise. Moreover, various scales and values may be used to define the clinical significance. In example embodiments, the clinical significance values may be configurable by one or more of the participating entities, such as a pharmacy or healthcare provider, or by any other entity, such as a standards setting authority or a regulatory agency.

Participating entities may elect to ignore or not process clinical significance, and in these cases, processing at block 602 could be ignored. Similarly, in cases in which there are no existing dosage error pairs, or where dosage error pair processing was not performed, clinical significance processing at block 602 may not be performed. Moreover, clinical significance determinations may be performed separately from typical dosage processing, and may optionally be performed in combination with other dosage verification processing described herein, such as in embodiments described with reference to FIGS. 3 and 4.

Following block 602 is block 604, in which the dosage verification module may determine the most common daily dosage ("MCDD") values for the submitted drug product. At block 606, common daily dosage ("CDD") values are determined for the submitted drug product. MCDD values and CDD values may be determined at blocks 604 and 608 by consulting a lookup table or other suitable data structure (e.g., stored in a database) containing such information.

The commonly owned U.S. patent application Ser. No. 10/339,230 entitled "Systems and Methods for Look-Alike Sound-Alike Medication Error Messaging" describes in more detail various example techniques of determining MCDD and CDD values.

At step 608 a determination is made as to whether the submitted daily dosage is equal to the MCDD for the submitted drug product. If the submitted daily dosage is equal to the MCDD for the submitted drug product, the method moves to step 610, where the dosage verification module may not set an indicator or otherwise set an edit action to not perform an action. Following step 610, the method may end.

However, if it is determined at step 608 that the submitted daily dosage is not equal to the MCDD for the submitted drug product, the method may proceed to step 612, where a determination is made as to whether the submitted daily dosage is equal to the CDD for the submitted drug product. If the submitted daily dosage is equal to the CDD for the submitted drug product, the method moves to step 610, where the dosage verification module may not set an indicator or otherwise set an edit action to not perform an action. Following step 610, the method may end.

However, if it is determined at step 612 that the submitted daily dosage is not equal to the CDD for the submitted drug product, the method may proceed to step 614, to determine an edit action, or otherwise set an indicator, for a submitted daily dosage that does not satisfy both of the MCDD and the CDD values for the submitted drug product. Not satisfying the MCDD and the CDD values for the submitted drug product may indicate that a potential strength error has been submitted in the prescription transaction. In other embodiments, satisfying only one, but not the other, such as satisfying the CDD but not the MCDD, may also cause a typical dosing indicator to be set by the dosage verification module and a corresponding edit action to be performed.

In one embodiment, the edit action performed and/or the message or messages generated or data stored may also depend upon the clinical significance, such as is optionally determined in block 602. Moreover, the messages generated or data stored may further include typical dosage values determined during the typical dosage processing, such as the MCDD or CDD values. Submitting these values may give the pharmacy (or other entity) better information for determining whether the submitted strength is in fact an error or not.

Accordingly, with reference to the example methods illustrated in FIGS. 3-6, systems and methods provide dosage verification processing for determining whether a submitted prescription transaction potentially includes a drug strength error. As illustrated, various processing steps may be performed alone or in combination to aid in the determination of whether the submitted strength is likely an error. For example, in one embodiment, only dosage error pair processing is performed to set an error indicator and perform the appropriate edit action. In another embodiment, only the patient history may be reviewed to determine whether the same or similar prescription has been previously prescribed to the patient, with the outcome determining whether the submitted drug strength is potentially an error. In yet other embodiments, absolute dosage processing or typical dosage processing may be performed separately from the example dosage error pair processing to facilitate identifying a potential drug strength error. Accordingly, the example methods illustrated herein are not intended to be limiting, and various embodiments may include or exclude some or all of the steps and/or determinations illustrated therein. Moreover, to promote the reliability of dosage verification processing, such as to reduce false positives or limit the volume of messages received, participating entities (such as pharmacies of service providers) may configure or otherwise customize the dosage verification processing and resulting edit actions to suit their needs and messaging tolerances, as further described herein.

FIG. 7 is a flowchart illustrating an example method 700 for creating and/or updating a patient history database, according to one example embodiment. As described with reference to FIGS. 2-4, a patient history database may be maintained and accessed during dosage verification processing, such as to determine whether a patient has previously been prescribed the same or similar drug product and strength combination, or to determine whether the patient's physical traits (e.g., sex, age, weight, height) or medical history suggest the submitted strength may be incorrect for that patient.

The method 700 begins at block 702, in which a service provider may receive a prescription transaction in a manner similar to that described with reference to FIG. 3. Following block 702 is block 704, in which the prescription transaction is parsed to extract prescription data and/or patient data from the transaction. For example, at least a patient identifier, the submitted drug product, the submitted drug strength are extracted. In embodiments, additional data may be extracted from the prescription transaction, including, but not limited to, patient information, such as name, gender, patient address, and patient contact information, insurance/coverage information, such as cardholder name, cardholder identifier, and effective date, prescriber information, such as primary care identifier, primary care provider name, prescriber identifier, prescriber name, and prescriber contact information, pharmacy information, such as pharmacy contact information, and pharmacy identifier, and prescription information, such as date prescription written, quantity dispensed, number of days supply, diagnosis/condition, pricing information, and date of service.

After extracting data from the prescription transaction, decision block 706 may follow, in which it is determined whether the transaction is for a prescription claim reversal or for a prescription request transaction (e.g., prescription claim for a new or refill prescription).

If it is identified at block 706 that the prescription transaction is not for a reversal, block 708 follows. At block 708, additional patient information may optionally be captured. For example, if this is the first time a prescription has been received for a given patient, while building the patient history database, the service provider may obtain patient specific information, such as, but not limited to, patient date of birth/age, patient age, patient sex, patient height, patient weight, known ailments or other medical conditions (past and existing), and the like. In example embodiments, the pharmacy computer may be operable for transmitting the additional patient information. Though, in other embodiments, the service provider may request or otherwise obtain the information from other sources, such as, but not limited to, a payer associated with the patient (e.g., insurer), directly from the patient, from the prescribing physician or other healthcare provider, from a third party service provider, and the like.

Following block 708 is block 710, in which the service provider may determine that the prescription transaction has been approved prior to updating data stored in the patient history database. In one example, the service provider may obtain an approval message or other authorization from a payer, such as when a prescription claim is transmitted to a payer for authorization before filling. In another example, the service provider may perform its own verification processing, such as is described herein to verify dosage amounts, or as otherwise may be performed in association with pre- or post-processing editing. In yet another example, the service provider may wait to update patient history data until it has received an indication from the pharmacy that the respective prescription has actually been disbursed to the patient.

After determining that the prescription transaction is approved or otherwise a valid prescription transaction, block 712 may follow, in which one or more records in the patient history database are entered and/or updated to reflect the received prescription transaction. In one embodiment, a record may be created that includes, but is not limited to, the prescribed drug product and strength (both of which may be stored separately by name or the combination referenced by NDC# or by another identifier), dosage information (e.g., days supply, quantity, etc.), and a patient identifier to associate the prescription transaction record with other patient information that may optionally be maintained by the patient history database. In certain embodiments, the patient history database may further include one or more dates associated with the prescription, such as a date written, date approved, date disbursed, etc., which may optionally be used to restrict the history reviewed for the patient when performing dosage verification processing. Any other information as may be transmitted and/or extracted from a prescription transaction record may be stored in the patient history database and associated with the respective patient and prescription transaction.

Accordingly, capturing prescription data and storing it in a patient history database associated with the patient can provide a helpful resource for processing prescription transactions. As described herein, a specific patient's historical prescription transactions may be used to verify subsequent prescription transactions. In other embodiments, historical patient data for a group of patients may be used as a data set from which statistically-determined criteria (e.g., MCDD or CDD) can be determined. Moreover, patient history data can be used by the service provider to perform subsequent analyses, such as, but not limited to, error checking, prescription matching, performance reporting, auditing, and the like.

The method may end after block 712, having updated the patient history database with prescription and/or patient data from the respective transaction.

However, if at block 706 it is determined that the prescription transaction is for a reversal transaction, block 714 follows. At block 714, the service provider may remove the corresponding prescription transaction from the patient history database, such that the database only reflects valid, actual prescriptions, and does not include prescription transactions that have been reversed for whatever reason. In various embodiments, the reversed prescription transaction record may be inactivated, deleted, or otherwise indicated as a reversal, such that the record may not be considered when reviewing patient history data.

In one example embodiment, the service provider may transmit the reversal to a payer (or other entity) to obtain approval before reversing the records in the patient history database.

The method may end after block 714, having updated the patient history database to remove or otherwise exclude prescription data from the patient history database for the respective reversal transaction.

It will be appreciated that the example aspects and features described herein are not intended to be interpreted as required or essential elements of the various embodiments, unless explicitly stated as such. It will also be appreciated that the foregoing description of example embodiments is provided by way of illustration only and that many other modifications, features, embodiments, and operating environments are possible. For example, the subject matter described herein is not intended to be limited to the prescription transaction or claim editing environment. In other embodiments, one or more of the dosage verification processes can be readily adapted for application in electronic prescription systems, hospital inpatient medication ordering systems, physician management systems, claim adjudication and processing systems, and the like.

Embodiments of the invention have been described herein with reference to block diagrams and flowchart illustrations of systems, methods, apparatus, and computer program products according to various example embodiments. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, processor, or other programmable data processing apparatus to produce a particular machine, such that the instructions which are executed on or by the computer or other programmable data processing apparatus create means for implementing the particular functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks.

Accordingly, blocks of the block diagrams and flowchart illustrations support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Many modifications and other embodiments will come to mind having the benefit of the teachings presented in this description and the associated drawings. Therefore, it will be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system for dosage error verification of unit strength errors, comprising:
   means for receiving prescription data relating to a prescription;
   at least one database storing data of unit strength error pairs; and
   a processor functionally coupled to the means for receiving prescription data and the at least one database, and configured for executing computer program instructions to:
   receive a prescription transaction comprising a submitted drug product and a submitted strength of the submitted drug product;
   compare the submitted drug product and the submitted strength to unit strength error data residing in an error database;
   determine that the submitted drug product is a member of at least one error pair indicated by the error data;
   determine that the submitted strength is potentially incorrect based at least in part on strengths indicated by the at least one error pair, wherein the error pair comprises counterpart strengths for the drug product known to cause dispensing errors; and
   perform an edit action based at least in part on the determination that the submitted strength is potentially incorrect.

2. The system of claim 1, wherein the processor is further operable to execute the computer program instructions to perform the edit action by:
   generating a message; and
   transmitting the message.

3. The system of claim 2, wherein the message comprises at least one of: a suggested strength, a suggested drug product, the submitted drug product, or the submitted strength.

4. The system of claim 1, wherein the processor is further operable to execute the computer program instructions to perform the edit action by:
   generating a prescription transaction rejection; and
   transmitting the prescription transaction rejection.

5. The system of claim 1, wherein the processor is further operable to execute the computer program instructions to determine that the submitted strength is potentially incorrect by determining that the submitted strength does not represent a likely strength of the at least one error pair.

6. The system of claim 1, wherein the processor is further operable to execute the computer program instructions to determine that the submitted strength is potentially incorrect by determining that the submitted strength is indicated as an error strength by the error data.

7. The system of claim 1, wherein the prescription transaction identifies a patient to whom the submitted drug product is prescribed, and wherein the processor is further operable to execute the computer program instructions to determine that the submitted strength is potentially incorrect by:
   comparing the submitted drug product and the submitted strength to patient history data associated with the patient and residing in a patient history database; and
   determining that the submitted drug product and submitted strength has not previously been prescribed to the patient based on the patient history data for the patient.

8. The system of claim 1, wherein the processor is further operable to execute the computer program instructions to determine that the submitted strength is potentially incorrect by determining that a calculated daily dosage based on the submitted strength does not meet at least one of: maximum dosage criteria, minimum dosage criteria, or typical dosage criteria.

9. The system of claim 1, wherein the processor is further operable to execute the computer program instructions to store error data associated with the submitted drug product and submitted strength.

10. The system of claim 1, wherein the processor is further operable to execute the computer program instructions to edit the submitted strength responsive at least in part to determining that the submitted strength represents an error strength of the at least one error pair, wherein the submitted strength is altered to a likely strength of the at least one error pair.

11. The system of claim 1, wherein the processor is further operable to execute the computer program instructions to build a patient history database, wherein the patient history database comprises records indicating historical prescription transactions for a plurality of patients.

12. The system of claim 11, wherein the prescription transaction identifies a patient to whom the submitted drug product is prescribed, and wherein the processor is further operable to execute the computer program instructions to store information associated with the prescription transaction in the patient history database associated with the patient.

13. The system of claim 1, wherein the processor is further operable to execute the computer program instructions to build the error database.

14. The system of claim 13, wherein the processor is further operable to execute the computer program instructions to store data associated with historical prescription transactions containing at least one unit strength error.

15. The system of claim 13, wherein the processor is further operable to execute the computer program instructions to build the error database by identifying a plurality of error pairs, wherein each member of each error pair comprises a drug product and drug strength, and wherein one drug strength of the in the drug pair represent a likely error of the other drug strength.

16. The system of claim 15, wherein the likely error results from at least one of: a multiple of ten, has a single digit difference, a trailing zero after a decimal point, no leading zero before a decimal point, a character misidentification as a digit of a strength, or a spoken similarity.

17. The system of claim 15, wherein the likely error is indicated as a result of at least one of: a historical analysis of dosage errors or a statistical analysis of dosage errors.

18. A method for verification of unit strength errors, comprising:
receiving a prescription transaction comprising a submitted drug product and a submitted strength of the submitted drug product;
comparing the submitted drug product and the submitted strength to data of unit strength error pairs residing in an error database;
determining that the submitted drug product is a member of at least one error pair indicated by the error data;
determining that the submitted strength is potentially incorrect based at least in part on strengths indicated by the at least one error pair, wherein the error pair comprises counterpart strengths for the drug product known to cause dispensing errors; and
performing an edit action based at least in part on the determination that the submitted strength is potentially incorrect;
wherein the prior steps are performed by one or more computer processors executing computer-executable instruction.

19. The method of claim 18, wherein determining that the submitted strength is potentially incorrect further comprises determining that the submitted strength does not represent a likely strength of the at least one error pair.

20. The method of claim 18, wherein determining that the submitted strength is potentially incorrect further comprises determining that the submitted strength is indicated as an error strength by the error data.

21. The method of claim 18, wherein the prescription transaction identifies a patient to whom the submitted drug product is prescribed, and wherein determining that the submitted strength is potentially incorrect further comprises:
comparing the submitted drug product and the submitted strength to patient history data associated with the patient and residing in a patient history database; and
determining that the submitted drug product and submitted strength has not previously been prescribed to the patient based on the patient history data for the patient.

22. The method of claim 18, wherein determining that the submitted strength is potentially incorrect further comprises determining that a calculated daily dosage based on the submitted strength does not meet at least one of: maximum dosage criteria, minimum dosage criteria, or typical dosage criteria.

23. The method of claim 18, further comprising building a patient history database, wherein the patient history database comprises records indicating historical prescription transactions for a plurality of patients.

24. A system for unit strength error verification, comprising:
means for receiving prescription data relating to a prescription;
at least one database storing patient history data; and
a processor functionally coupled to the means for receiving prescription data and the at least one database, and configured for executing computer program instructions to:
receive a prescription transaction comprising a submitted drug product, a submitted strength of the submitted drug product, and identifying a patient to whom the submitted drug product is prescribed;
determine that the submitted drug product is a member of at least one error pair indicated by error data residing in a dosage error database, wherein the error pair comprises counterpart strengths for the drug product known to cause dispensing errors;
compare the submitted drug product and the submitted strength to patient history data associated with the patient and residing in a patient history database;
determine that the submitted strength is potentially incorrect based at least in part on the patient history data associated with the patient; and
perform an edit action based on the determination that the submitted strength is potentially incorrect.

25. The system of claim 24, wherein the processor is further operable to execute the computer program instructions to determine that the submitted strength is potentially incorrect by determining that the submitted drug product has been previously prescribed to the patient, but that the submitted drug product has not been prescribed to the patient in the submitted strength.

26. The system of claim 24, wherein the processor is further operable to execute the computer program instructions to determine that the submitted strength is potentially incorrect by determining that the submitted drug product has not been previously prescribed to the patient.

27. The system of claim 24, wherein the processor is further operable to execute the computer program instructions to determine that the submitted strength is potentially incorrect by determining that the prescription transaction is not a prescription refill transaction.

28. A method for unit strength verification, comprising executing computer program instructions by one or more processors for:
receiving a prescription transaction comprising a submitted drug product, a submitted strength of the submitted drug product, and identifying a patient to whom the submitted drug product is prescribed;
determining that the submitted drug product is a member of at least one error pair indicated by dosage error data residing in an error database, wherein the error pair comprises counterpart strengths for the drug product known to cause dispensing errors;
comparing the submitted drug product and the submitted strength to patient history data associated with the patient and residing in a patient history database;
determining that the submitted strength is potentially incorrect based at least in part on the patient history data associated with the patient; and
performing an edit action based on the determination that the submitted strength is potentially incorrect;
wherein the prior steps are performed by one or more computer processors executing computer-executable instruction.

* * * * *